United States Patent
Bray et al.

(10) Patent No.: US 12,077,607 B2
(45) Date of Patent: Sep. 3, 2024

(54) FUNCTIONAL AND THERAPEUTIC EFFECTS OF PAR4 CLEAVAGE BY CATHEPSIN G

(71) Applicant: UNIVERSITY OF UTAH RESEARCH FOUNDATION, Salt Lake City, UT (US)

(72) Inventors: Paul F. Bray, Salt Lake City, UT (US); Robert A. Campbell, Salt Lake City, UT (US); Michelle Stoller, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/934,816

(22) Filed: Sep. 23, 2022

(65) Prior Publication Data
US 2023/0126796 A1 Apr. 27, 2023

Related U.S. Application Data

(60) Provisional application No. 63/247,636, filed on Sep. 23, 2021.

(51) Int. Cl.
*C07K 7/06* (2006.01)
*A61P 7/04* (2006.01)
*A61K 38/00* (2006.01)

(52) U.S. Cl.
CPC .......... *C07K 7/06* (2013.01); *A61P 7/04* (2018.01); *A61K 38/00* (2013.01)

(58) Field of Classification Search
CPC ................... A61K 38/08; C07K 7/06
See application file for complete search history.

(56) References Cited

U.S. PATENT DOCUMENTS

| | | | | |
|---|---|---|---|---|
| 5,877,153 A * | 3/1999 | Harris | ............. | C07K 14/001 514/21.4 |
| 7,122,342 B1 | 10/2006 | Xu et al. | | |
| 8,445,448 B2 * | 5/2013 | Wraith | ............. | C07K 14/755 514/14.1 |
| 9,605,024 B2 | 3/2017 | Kornacker et al. | | |
| 10,822,343 B2 | 11/2020 | Banville et al. | | |
| 2020/0190496 A1 | 6/2020 | Steward et al. | | |

FOREIGN PATENT DOCUMENTS

| | | | | |
|---|---|---|---|---|
| WO | WO-9950415 A2 * | 10/1999 | ........... | C07K 14/705 |
| WO | 2001060401 A1 | 8/2001 | | |
| WO | 2017075537 A1 | 5/2017 | | |

OTHER PUBLICATIONS

French et al. "Protease-activated receptor 4: from structure to function and back again", British Journal of Pharmacology (2016) 173 2952-2965 (Year: 2016).*
Asfaha et al., Protease-activated receptor-4: a novel mechanism of inflammatory pain modulation, Br J Pharmacol., 2007, pp. 176-185 (Year: 2007).*
Kahn et al. "The Physical Associated of the P2Y12 Receptor with PAR4 Regulates Arrestin-Mediated Akt Activation", Molecular Pharmacology, 2014, pp. 1-11 (Year: 2014).*
Holinstat et al., "PAR4, but not PAR1, Signals Human Platelet Aggregation via Ca2+ Mobilization and Synergistic P2Y12 Receptor Activation", JBC, 2006, pp. 26665-26674 (Year: 2006).*
Thibeault P.E. et al., Molecular basis for activation and biased signaling at the thrombin-activated GPCR proteinase activated receptor-4 (PAR4). J Biol Chem 295, 2520-2540 (2020).
Thorpe M. et al. Extended cleavage specificity of human neutrophil cathepsin G: A low activity protease with dual chymase and tryptase-type specificities. PLoS One 13, e0195077 (2018).
Tognetto M, et al. Evidence that PAR-1 and PAR-2 mediate prostanoid-dependent contraction in isolated guinea-pig gallbladder. Br J Pharmacol. 2000;131(4):689-94.
Tourdot BE, et al. "Mechanism of race-dependent platelet activation through the protease-activated receptor-4 and Gq signaling axis." Arteriosclerosis, thrombosis, and vascular biology 34.12 (2014): 2644-2650.
Tourdot BE, et al. Genetic Variant in Human PAR (Protease-Activated Receptor) 4 Enhances Thrombus Formation Resulting in Resistance to Antiplatelet Therapeutics. Arteriosclerosis, thrombosis, and vascular biology. 2018;38 (7):1632-43.
Tricoci P, et al. Effects of genetic variation in protease activated receptor 4 after an acute coronary syndrome: Analysis from the TRACER trial. Blood Cells Mol Dis. 2018;72:37-43.
Tricoci P, et al. Thrombin-receptor antagonist vorapaxar in acute coronary syndromes. The New England journal of medicine. 2012;366(1):20-33.
Van Eeuwijk JM, et al. The Novel Oral Syk Inhibitor, BI1002494, Protects Mice From Arterial Thrombosis and Thromboinflammatory Brain Infarction. Arteriosclerosis, thrombosis, and vascular biology. 2016;36(6):1247-53.
Vergnolle N, et al. Characterization of thrombin-induced leukocyte rolling and adherence: a potential proinflammatory role for proteinase-activated receptor-4. J Immunol. 2002;169(3):1467-73.
Verhenne S, et al. Platelet-derived VWF is not essential for normal thrombosis and hemostasis but fosters ischemic stroke injury in mice. Blood. 2015;126(14):1715-22.
Walsh MT, et al. The alpha, but not the beta, isoform of the human thromboxane A2 receptor is a target for prostacyclin-mediated desensitization. J Biol Chem. 2000;275(27):20412-23.
Wang J, et al. A simple protocol for isolating mouse lung endothelial cells. Sci Rep. 2019;9(1):1458.
Warach S, et al. Evidence of reperfusion injury, exacerbated by thrombolytic therapy, in human focal brain ischemia using a novel imaging marker of early blood-brain barrier disruption. Stroke. 2004;35(11 Suppl 1):2659-61.

(Continued)

*Primary Examiner* — Lianko G Garyu
(74) *Attorney, Agent, or Firm* — Michael Best & Friedrich LLP

(57) ABSTRACT

Disclosed herein are a synthetic peptide mimetic and compositions comprising the synthetic peptide mimetic that induce activation of and signaling through PAR4. Also disclosed herein are methods of treating a bleeding disorder comprising administering the synthetic peptide.

13 Claims, 20 Drawing Sheets

Specification includes a Sequence Listing.

(56) References Cited

OTHER PUBLICATIONS

Weksler, B. B., et al. "Human leukocyte cathepsin G and elastase specifically suppress thrombin-induced prostacyclin production in human endothelial cells." (1989): 1627-1634.
Welser-Alves JV, et al. Isolation and culture of primary mouse brain endothelial cells. Methods Mol Biol. 2014;1135:345-56.
Whitley MJ, et al. The protease-activated receptor 4 Ala120Thr variant alters platelet responsiveness to low-dose thrombin and protease-activated receptor 4 desensitization, and is blocked by non-competitive P2Y12 inhibition. Journal of thrombosis and haemostasis : JTH. 2018; 16(12):2501-14.
Wilson SJ, et al. Dimerization of the human receptors for prostacyclin and thromboxane facilitates thromboxane receptor-mediated cAMP generation. J Biol Chem. 2004;279(51):53036-47.
Wilson SJ, et al. PAR4 (Protease-Activated Receptor 4) Antagonism With BMS-986120 Inhibits Human Ex Vivo Thrombus Formation. Arteriosclerosis, thrombosis, and vascular biology. 2018;38(2):448-56.
Wu Y, et al. Highly efficient therapeutic gene editing of human hematopoietic stem cells. Nature medicine. 2019;25 (5):776-83.
Yamauchi K, et al. Effects of ticagrelor in a mouse model of ischemic stroke. Sci Rep. 2017;7(1):12088.
Yee, D.L. et al., Platelet hyperreactivity generalizes to multiple forms of stimulation. J Thromb Haemost 4, 2043-2050 (2006).
Yilmaz G, et al. Cell adhesion molecules and ischemic stroke. Neurol Res. 2008;30(8):783-93.
Yost CC, et al. Impaired neutrophil extracellular trap (NET) formation: a novel innate immune deficiency of human heonates. Blood. 2009;113(25):6419-27.
Yost CC, et al. Neonatal NET-inhibitory factor and related peptides inhibit neutrophil extracellular trap formation. J Clin Invest. 2016;126(10):3783-98.
Yuan Y, et al. Neutrophil macroaggregates promote widespread pulmonary thrombosis after gut ischemia. Sci Transl Med. 2017;9(409) 1-14.
Zeller, J.A. et al., Circulating platelets show increased activation in patients with acute cerebral ischemia. Thromb Haemost 81, 373-377 (1999).
Zhang C, et al. High-resolution crystal structure of human protease-activated receptor 1. Nature. 2012;492 (7429):387-92.
Zhao P. et al. Neutrophil Elastase Activates Protease-activated Receptor-2 (PAR2) and Transient Receptor Potential Vanilloid 4 (TRPV4) to Cause Inflammation and Pain. J Biol Chem 290, 13875-13887 (2015).
Eagle, K. A., et al. "Identifying patients at high risk of a cardiovascular event in the near future: current status and future directions: report of a national heart, lung, and blood institute working group." Circulation 121.12 (2010): 1447-1454.
Edelstein L.C. et al., Common variants in the human platelet PAR4 thrombin receptor alter platelet function and differ by race. Blood 124, 3450-3458 (2014).
Edelstein L.C. et al., Racial differences in human platelet PAR4 reactivity reflect expression of PCTP and miR-376c. Nat Med 19, 1609-1616 (2013).
Edelstein LC, et al. Human genome-wide association and mouse knockout approaches identify platelet supervillin as an inhibitor of thrombus formation under shear stress. Circulation. 2012;125(22):2762-71.
Elwood P. C. et al., Ischemic heart disease and platelet aggregation. The Caerphilly Collaborative Heart Disease Study. Circulation 83, 38-44 (1991).
Enzmann G, et al. Ischemia-reperfusion injury in stroke: impact of the brain barriers and brain immune privilege on neutrophil function. Ther Adv Neurol Disord. 2018; 11:1756286418794184 (15 pages).
Evangelista, V. et al. Platelet activation by fMLP-stimulated polymorphonuclear leukocytes: the activity of cathepsin G is not prevented by antiproteinases. Blood 77, 2379-2388 (1991).

Faraday N. et al., Cathepsin G-dependent modulation of platelet thrombus formation in vivo by blood neutrophils. PLoS One 8, e71447 (2013).
Faraday N. et al., Prospective evaluation of the relationship between platelet-leukocyte conjugate formation and recurrent myocardial ischemia in patients with acute coronary syndromes. Platelets 15, 9-14 (2004).
Faruqi TR, et al. Structure-function analysis of protease-activated receptor 4 tethered ligand peptides. Determinants of specificity and utility in assays of receptor function. J Biol Chem. 2000;275(26):19728-34.
Feistritzer C, et al. Endothelial barrier protection by activated protein C through PAR1-dependent sphingosine 1-phosphate receptor-1 crossactivation. Blood. 2005;105(8):3178-84.
Finigan JH, et al. Activated protein C mediates novel lung endothelial barrier enhancement: role of sphingosine 1-phosphate receptor transactivation. J Biol Chem. 2005;280(17):17286-93.
Fisher M, et al. Cerebral microbleeds in the elderly: a pathological analysis. Stroke. 2010;41(12):2782-5.
Flossmann E, et al. Systematic review of methods and results of studies of the genetic epidemiology of ischemic stroke. Stroke. 2004;35(1):212-27.
Fluri F, et al. Animal models of ischemic stroke and their application in clinical research. Drug Des Devel Ther. 2015;9:3445-54.
French S.L. et al., A function-blocking PAR4 antibody is markedly antithrombotic in the face of a hyperreactive PAR4 variant. Blood Adv 2, 1283-1293 (2018).
French SL, et al. Humanizing the Protease-Activated Receptor (PAR) Expression Profile in Mouse Platelets by Knocking PAR1 into the Par3 Locus Reveals PAR1 Expression Is Not Tolerated in Mouse Platelets. PLoS One. 2016; 11(10):e0165565.
French SL, Hamilton JR. Protease-activated receptor 4: from structure to function and back again. British Journal of Pharmacology. 2016: 2952-2965.
French, S. L., et al. "Inhibition of protease-activated receptor 4 impairs platelet procoagulant activity during thrombus formation in human blood." Journal of Thrombosis and Haemostasis 14.8 (2016): 1642-1654.
Frey AJ, et al. Biased suppression of TP homodimerization and signaling through disruption of a TM GxxxGxxxL helical interaction motif. J Lipid Res. 2013;54(6):1678- 90.
Fukushima N, et al. Melittin, a metabostatic peptide inhibiting Gs activity. Peptides. 1998; 19(5):811-9.
Fuster V, et al. Plaque rupture, thrombosis, and therapeutic implications. Haemostasis. 1996;26 Suppl 4:269-284.
Fuster, V. et al. The pathogenesis of coronary artery disease and the acute coronary syndromes (1). New England Journal of Medicine 326, 242-250 (1992).
Gether, U. et al. G protein-coupled receptors. II. Mechanism of agonist activation. The Journal of biological chemistry 273, 17979-17982 (1998).
Giles JA, et al. Neutrophil infiltration to the brain is platelet-dependent, and is reversed by blockade of platelet GPIbalpha. Immunology. 2018;154(2):322-8.
Giovanazzi S, et al. Internalization and down-regulation of the prostacyclin receptor in human platelets. Biochem J. 1997;325 ( Pt 1):71-7.
Govekar, R., et al. "Eryptotic phenotype in chronic myeloid leukemia: contribution of neutrophilic cathepsin G." Anemia 2012 (2012) 659303.
Grau AJ, et al. Leukocyte count as an independent predictor of recurrent ischemic events. Stroke. 2004;35 (5):1147-52.
Gregory, A. D., et al. "Clathrin pit-mediated endocytosis of neutrophil elastase and cathepsin G by cancer cells." Journal of Biological Chemistry 287.42 (2012): 35341-35350.
Grisolano, J. L., et al. "Altered myeloid development and acute leukemia in transgenic mice expressing PML-RARa under control of cathepsin G regulatory sequences." Blood, The Journal of the American Society of Hematology 89.2 (1997): 376-387.
Gschwendtner A, et al. Sequence variants on chromosome 9p21.3 confer risk for atherosclerotic stroke. Annals of neurology. 2009;65(5):531-9.

(56) References Cited

OTHER PUBLICATIONS

Guan, X., et al. "The crosstalk between cancer cells and neutrophils enhances hepatocellular carcinoma metastasis via neutrophil extracellular traps-associated Cathepsin G component: a potential therapeutic target." Journal of Hepatocellular Carcinoma 8 (2021): 451-465.
Hamilton, J.R. et al., Increased expression of protease-activated receptor-2 (PAR2) and PAR4 in human coronary artery by inflammatory stimuli unveils endothelium-dependent relaxations to PAR2 and PAR4 agonists. Circ Res 89, 92-98 (2001).
Hamilton, J.R. et al., Protease-activated receptor (PAR) 1 but not PAR2 or PAR4 mediates endothelium-dependent relaxation to thrombin and trypsin in human pulmonary arteries. Journal of Cardiovascular Pharmacology 38, 108-119 (2001).
Han X. et al., PAR4 activation involves extracellular loop 3 and transmembrane residue Thr153. Blood 136, 2217-2228 (2020).
Han, N., et al. "Protease-activated receptors in cancer: A systematic review." Oncology letters 2.4 (2011): 599-608.
Hansen, K.K. et al. Tethered ligand-derived peptides of proteinase-activated receptor 3 (PAR3) activate PAR1 and PAR2 in Jurkat T cells. Immunology 112, 183-190 (2004).
Heckl D, et al. Generation of mouse models of myeloid malignancy with combinatorial genetic lesions using CRISPR-Cas9 genome editing. Nat Biotechnol. 2014;32(9):941-6.
Hedna VS, et al. Validity of Laser Doppler Flowmetry in Predicting Outcome in Murine Intraluminal Middle Cerebral Artery Occlusion Stroke. J Vasc Interv Neurol. 2015;8(3):74-82.
Hein L, et al. Intracellular targeting and trafficking of thrombin receptors. A novel mechanism for resensitization of a G protein-coupled receptor. J Biol Chem. 1994;269(44):27719-26.
Henriksen, R.A. et al. "PAR-4 agonist AYPGKF stimulates thromboxane production by human platelets." Arteriosclerosis, thrombosis, and vascular biology 22.5 (2002): 861-866.
Herrmann SM, et al. Characterization of polymorphic structure of cathepsin G gene: role in cardiovascular and cerebrovascular diseases. Arteriosclerosis, thrombosis, and vascular biology. 2001;21(9):1538-43.
Holinstat M. et al., PAR4, but not PAR1, signals human platelet aggregation via Ca2+ mobilization and synergistic P2Y12 receptor activation. J Biol Chem 281, 26665-26674 (2006).
Holinstat, M. et al. Protease receptor antagonism to target blood platelet therapies. Clin Pharmacol Ther 99, 72-81 (2016).
Holliday EG, et al. Common variants at 6p21.1 are associated with large artery atherosclerotic stroke. Nat Genet. 2012;44(10):1147-51.
Horne BD, et al. Which white blood cell subtypes predict increased cardiovascular risk? J Am Coll Cardiol. 2005;45 (10):1638-43.
Howard VJ, et al. Disparities in stroke incidence contributing to disparities in stroke mortality. Annals of neurology. 2011;69(4):619-27.
Husten, L. FDA Advisory Panel Votes In Favor Of Approval For Merck's Vorapaxar. Jan. 15, 2014. Available online at https://www.forbes.com/sites/larryhusten/2014/01/15/fda-advisory-panel-votes-in-favor-of-approval-for-mercks-vorapaxar/?sh=7cff52a9eb55 (2 pages).
Ikram MA, et al. Genomewide association studies of stroke. The New England journal of medicine. 2009;360 (17):1718-28.
Jamieson GA. Pathophysiology of platelet thrombin receptors. Thrombosis and Haemostasis. 1997;78(1):242-6.
Jenie RI, et al. Increased ubiquitination and the crosstalk of G protein signaling in cardiac myocytes: involvement of Ric-8B in Gs suppression by Gq signal. Genes Cells. 2013; 18(12):1095-106.
Jin, W., et al. "AML1-ETO targets and suppresses cathepsin G, a serine protease, which is able to degrade AML1-ETO in t (8; 21) acute myeloid leukemia." Oncogene 32.15 (2013): 1978-1987.
Jones RL, et al. Investigation of the prostacyclin (IP) receptor antagonist RO1138452 on isolated blood vessel and platelet preparations. Br J Pharmacol. 2006; 149(1):110-20.
Kahn ML, et al. A dual thrombin receptor system for platelet activation. Nature. 1998;394(6694):690-4.
Kahn ML, et al. Protease-activated receptors 1 and 4 mediate activation of human platelets by thrombin. J Clin Invest. 1999;103(6):879-87.
Kaplan ZS, et al. Thrombin-dependent intravascular leukocyte trafficking regulated by fibrin and the platelet receptors GPIb and PAR4. Nat Commun. 2015;6:7835.
Keller, A., et al. "Empirical statistical model to estimate the accuracy of peptide identifications made by MS/MS and database search." Analytical chemistry 74.20 (2002): 5383-5392.
Kernan WN, et al. Guidelines for the prevention of stroke in patients with stroke and transient ischemic attack: a guideline for healthcare professionals from the American Heart Association/American Stroke Association. Stroke. 2014;45(7):2160-236.
Khan A, et al. The physical association of the P2Y12 receptor with PAR4 regulates arrestin-mediated Akt activation. Mol Pharmacol. 2014;86(1):1-11.
Khan, M., et al. "Cathepsin G is expressed by acute lymphoblastic leukemia and is a potential immunotherapeutic target." Frontiers in immunology 8 (2018): 1975.
Kim SW, et al. Neutrophil extracellular trap induced by HMGB1 exacerbates damages in the ischemic brain. Acta Neuropathol Commun. 2019;7(1):94.
Kirkpatrick AC, et al. Coated-platelets predict stroke at 30 days following TIA. Neurology. 2017;89(2):125-8.
Kirkpatrick AC, et al. Higher Coated-Platelet Levels in Acute Stroke are Associated with Lower Cognitive Scores at Three Months Post Infarction. J Stroke Cerebrovasc Dis. 2019;28(9):2398-406.
Kissela B, et al. Stroke in a biracial population: the excess burden of stroke among blacks. Stroke. 2004;35 (2):426-31.
Kleindorfer D, et al. The unchanging incidence and case-fatality of stroke in the 1990s: a population-based study. Stroke. 2006;37(10):2473-8.
Ko JK, et al. Inducible RGS2 is a cross-talk regulator for parathyroid hormone signaling in rat osteoblast-like UMR106 cells. Biochem Biophys Res Commun. 2001;287(4):1025-33.
Korporaal SJA, et al. Peptide Antagonists for P-selectin Discriminate between Sulfatide-Dependent Platelet Aggregation and PSGL-1-Mediated Cell Adhesion. J Clin Med. 2019;8(8) (15 pages).
Kraemer BF, et al. Novel anti-bacterial activities of beta-defensin 1 in human platelets: suppression of pathogen growth and signaling of neutrophil extracellular trap formation. PLoS Pathog. 2011;7(11):e1002355.
Kudo, T., et al. "Cathepsin G, a neutrophil protease, induces compact cell-cell adhesion in MCF-7 human breast cancer cells." Mediators of inflammation 2009:850940.
Kuliopulos A, et al. Plasmin desensitization of the PAR1 thrombin receptor: kinetics, sites of truncation, and Implications for thrombolytic therapy. Biochemistry. 1999;38(14):4572-85.
Kyte, J. et al. "A simple method for displaying the hydropathic character of a protein." Journal of molecular biology 157.1 (1982): 105-132.
Lam, J. Y. et al., Platelet aggregation, coronary artery disease progression and future coronary events. The American journal of cardiology 73, 333-338 (1994).
Laridan E, et al. Neutrophil extracellular traps in ischemic stroke thrombi. Annals of neurology. 2017;82(2):223-32.
Larosa, C. A., et al. "Human neutrophil cathepsin G is a potent platelet activator." Journal of vascular surgery 19.2 (1994): 306-320.
Lee CD, et al. White blood cell count and incidence of coronary heart disease and ischemic stroke and mortality from cardiovascular disease in African-American and White men and women: atherosclerosis risk in communities study. Am J Epidemiol. 2001;154(8):758-764.
Lin H, et al. Cofactoring and dimerization of proteinase-activated receptors. Pharmacol Rev. 2013;65(4):1198-213.
Lisman, T. "Platelet-neutrophil interactions as drivers of inflammatory and thrombotic disease." Cell and tissue research 371.3 (2018): 567-576.
Liu HL, et al. Magnetic resonance imaging enhanced by superparamagnetic iron oxide particles: usefulness for distinguishing between focused ultrasound-induced blood-brain barrier disruption and brain hemorrhage. J Magn Reson Imaging. 2009;29(1):31-8.
Longa EZ, et al. Reversible middle cerebral artery occlusion without craniectomy in rats. Stroke. 1989;20(1):84-91.

(56) References Cited

OTHER PUBLICATIONS

Lova P. et al. Contribution of protease-activated receptors 1 and 4 and glycoprotein Ib-IX-V in the G(i)-independent activation of platelet Rap1B by thrombin. J Biol Chem 279, 25299-25306 (2004).

Ludeman MJ, et al. Regulated shedding of PAR1 N-terminal exodomain from endothelial cells. J Biol Chem. 2004;279(18):18592-9.

Macfarlane, S.R. et al. Proteinase-activated receptors. Pharmacological reviews 53, 245-282 (2001).

Mahajan-Thakur S. et al. Sphingosine-1-phosphate induces thrombin receptor PAR-4 expression to enhance cell migration and COX-2 formation in human monocytes. J Leukoc Biol 96, 611-618 (2014).

Maiocchi S, et al. Thromboinflammatory Functions of Platelets in Ischemia-Reperfusion Injury and Its Dysregulation In Diabetes. Semin Thromb Hemost. 2018;44(2):102-13.

Maksimowicz, T., et al. "Activity and tissue localization of cathepsin G in non small cell lung cancer." Roczniki Akademii Medycznej w Bialymstoku (1995) 42 (1997): 199-216.

Manne, B. K., et al. "Platelet gene expression and function in patients with COVID-19." Blood 136.11 (2020): 1317-1329.

Mao Y, et al. Deficiency of PAR4 attenuates cerebral ischemia/reperfusion injury in mice. J Cereb Blood Flow Metab. 2010;30(5):1044-52.

Maryanoff, B. E., et al. "Protease-activated receptor-2 (PAR-2): structure-function study of receptor activation by diverse peptides related to tethered-ligand epitopes." Archives of biochemistry and biophysics 386.2 (2001): 195-204.

Meschia JF, et al. Guidelines for the primary prevention of stroke: a statement for healthcare professionals from the American Heart Association/American Stroke Association. Stroke. 2014;45(12):3754-832.

Michelson AD, et al. Downregulation of the platelet surface glycoprotein Ib-IX complex in whole blood stimulated by thrombin, adenosine diphosphate, or an in vivo wound. Blood. 1991;77(4):770-9.

Middleton E.A. et al., Neutrophil extracellular traps contribute to immunothrombosis in COVID-19 acute respiratory distress syndrome. Blood 136, 1169-1179 (2020).

Miletich JP, et al. Properties of the factor Xa binding site on human platelets. J Biol Chem. 1978;253(19):6908-16.

Mirza H, et al. The proteinase activated receptor-2 (PAR-2) mediates mitogenic responses in human vascular endothelial cells. J Clin Invest. 1996;97(7):1705-14.

Mitchell JA, et al. Eicosanoids, prostacyclin and cyclooxygenase in the cardiovascular system. Br J Pharmacol. 2019;176(8):1038-50.

Molino M. et al. Proteolysis of the human platelet and endothelial cell thrombin receptor by neutrophil-derived cathepsin G. The Journal of biological chemistry 270, 11168-11175 (1995).

Moncada S, et al. Dipyridamole and other phosphodiesterase inhibitors act as antithrombotic agents by potentiating endogenous prostacyclin. Lancet. 1978;1(8077):1286-9.

Monroe DM, et al. Platelets and thrombin generation. Arteriosclerosis, thrombosis, and vascular biology. 2002;22 (9):1381-9.

Morimoto-Kamata, R. et al. "Insulin-like growth factor-1 signaling is responsible for cathepsin G-induced aggregation of breast cancer MCF-7 cells." Cancer science 108.8 (2017): 1574-1583.

Morimoto-Kamata, R., et al. "Cathepsin G induces cell aggregation of human breast cancer MCF-7 cells via a 2-step mechanism: catalytic site-independent binding to the cell surface and enzymatic activity-dependent induction of the cell aggregation." Mediators of inflammation 2012;2012:456462.

Morowski M, et al. Only severe thrombocytopenia results in bleeding and defective thrombus formation in mice. Blood. 2013;121(24):4938-47.

Abdalla, S. et al. "AT1-receptor heterodimers show enhanced G-protein activation and altered receptor sequestration." Nature 407.6800 (2000): 94-98.

Abrams CS, et al. Platelet Signal Transduction. In: Coleman RW, Marder, V.J., Clowes, A.W., George, J.N., Goldharber, S.Z., editor.

Hemostasis and Thrombosis. 5th ed. Philadelphia, PA: Lippincott Williams & Wilkins; 2006. p. 617-29.

Alatrash, G., et al. "Cathepsin G is broadly expressed in acute myeloid leukemia and is an effective Immunotherapeutic target." Leukemia 31.1 (2017): 234-237.

Alatrash, G., "Targeting cathepsin G in myeloid leukemia." Oncoimmunology 2.4 (2013): e23442.

Andon N.L. et al., Proteomic characterization of wheat amyloplasts using identification of proteins by tandem mass spectrometry. Proteomics 2, 1156-1168 (2002).

Antithrombotic Trialists Collaboration. Collaborative meta-analysis of randomised trials of antiplatelet therapy for prevention of death, myocardial infarction, and stroke in high risk patients. BMJ. 2002;324(7329):71-86.

Arachiche A, et al. Platelet specific promoters are insufficient to express protease activated receptor 1 (PAR1) transgene in mouse platelets. PLoS One. 2014;9(5):e97724.

Arbab-Zadeh, A., et al. "Acute coronary events." Circulation 125.9 (2012): 1147-1156.

Arehart E, et al. Acceleration of cardiovascular disease by a dysfunctional prostacyclin receptor mutation: potential Implications for cyclooxygenase-2 inhibition. Circ Res. 2008;102(8):986-93.

Atherton et al., "The Fluorenylmethoxycarbonyl Amino Protecting Group", in The Peptides: Analysis, Synthesis, Biology, vol. 9: "Special Methods in Peptide Synthesis, Part C", pp. 1-38, Undenfriend, S. et al., eds., Academic Press, San Diego, publ. (1987).

Attucci S. et al., Measurement of free and membrane-bound cathepsin G in human neutrophils using new sensitive fluorogenic substrates. Biochem J 366, 965-970 (2002).

Aveskogh, M. et al. Characterization of cDNA clones encoding mouse proteinase 3 (myeloblastine) and cathepsin G. Immunogenetics 46, 181-191 (1997).

Barak Ls, et al. Real-time visualization of the cellular redistribution of G protein-coupled receptor kinase 2 and beta-arrestin 2 during homologous desensitization of the substance P receptor. J Biol Chem. 1999;274(11):7565-9.

Barber Pa, et al. Temperature-regulated model of focal ischemia in the mouse: a study with histopathological and behavioral outcomes. Stroke. 2004;35(7):1720-5.

Basak I, et al. miR-15a-5p regulates expression of multiple proteins in the megakaryocyte GPVI signaling pathway. Journal of thrombosis and haemostasis : JTH. 2019;17(3):511-24.

Beck F, et al. Time-resolved characterization of cAMP/PKA-dependent signaling reveals that platelet inhibition is a concerted process involving multiple signaling pathways. Blood. 2014;123(5):e1-e10.

Bergmeier W, et al. Adoptive transfer method to study platelet function in mouse models of disease. Thromb Res. 2014;133 Suppl 1:S3-5.

Berlanga O, et al. Expression of the collagen receptor glycoprotein VI during megakaryocyte differentiation. Blood. 2000;96(8):2740-5.

Bevan S, et al. Genetic heritability of ischemic stroke and the contribution of previously reported candidate gene and genomewide associations. Stroke. 2012;43(12):3161-7.

Bhatlekar S, et al. Anti-apoptotic BCL2L2 increases megakaryocyte proplatelet formation in cultures of human cord blood. Haematologica. 2019 2075-2083.

Bhatlekar, S., et al. "miR-125a-5p regulates megakaryocyte proplatelet formation via the actin-bundling protein L-blastin." Blood 136.15 (2020): 1760-1772.

Bieber M, et al. Description of a Novel Phosphodiesterase (PDE)-3 Inhibitor Protecting Mice From Ischemic Stroke Independent From Platelet Function. Stroke. 2019;50(2):478-86.

Bley KR, et al., RO1138452 and RO3244794: characterization of structurally distinct, potent and selective IP (prostacyclin) receptor antagonists. Br J Pharmacol. 2006;147(3):335-45.

Bohm SK, et al. Mechanisms of desensitization and resensitization of proteinase-activated receptor-2. J Biol Chem. 1996;271(36):22003-16.

(56) References Cited

OTHER PUBLICATIONS

Bouchard BA, et al. Effector cell protease receptor-1, a platelet activation-dependent membrane protein, regulates prothrombinase-catalyzed thrombin generation. J Biol Chem. 1997;272(14):9244-51.

Brass LF, et al. Signal Transduction During Platelet Plug Formation. In: Michelson AD, editor. Platelets. Third ed: Elsevier; 2013. p. 367-98.

Bray PF, et al. Heritability of platelet function in families with premature coronary artery disease. Journal of thrombosis and haemostasis : JTH. 2007;5(8):1617-23.

Buck, B. H., et al. "Early neutrophilia is associated with vol. of ischemic tissue in acute stroke." Stroke 39.2 (2008): 355-360.

Campbell RA, et al. Contributions of extravascular and intravascular cells to fibrin network formation, structure, and stability. Blood. 2009;114(23):4886-96.

Campbell RA, et al. Human megakaryocytes possess intrinsic antiviral immunity through regulated induction of IFITM3. Blood. 2019;133(19):2013-26.

Campbell RA, et al. Interleukin 6 receptor alpha expression in PMNs isolated from prematurely born neonates: decreased expression is associated with differential mTOR signaling. Pediatr Res. 2019;86(1):55-62.

Chandler AB, et al. Coronary thrombosis in myocardial infarction. Report of a workshop on the role of coronary thrombosis in the pathogenesis of acute myocardial infarction. AmJ Cardiol. 1974;34(7):823-33.

Chen H, et al. Pleiotrophin produced by multiple myeloma induces transdifferentiation of monocytes into vascular endothelial cells: a novel mechanism of tumor-induced vasculogenesis. Blood. 2009; 113(9):1992-2002.

Clark RD, et al. Discovery and SAR development of 2-(phenylamino) imidazolines as prostacyclin receptor antagonists. Bioorg Med Chem Lett. 2004;14(4):1053-6.

Constantinescu-Bercu, A., et al. "Activated αIIbβ3 on platelets mediates flow-dependent NETosis via SLC44A2." Elife 9 (2020): e53353.

Coughlin S.R., Thrombin signalling and protease-activated receptors. Nature 407, 258-264 (2000).

Covic L, Gresser AL, Kuliopulos A. Biphasic kinetics of activation and signaling for PAR1 and PAR4 thrombin receptors in platelets. Biochemistry. 2000;39(18):5458-67.

Cremer S.E. et al., Proteomic profiling of the thrombin-activated canine platelet secretome (CAPS). PLoS One 14, e0224891 (2019).

Cumashi, A., et al. "Neutrophil proteases can inactivate human PAR3 and abolish the co-receptor function of PAR3 on murine platelets." Thrombosis and haemostasis 85.03 (2001): 533-538.

Dangwal S. et al. High glucose enhances thrombin responses via protease-activated receptor-4 in human vascular smooth muscle cells. Arteriosclerosis, thrombosis, and vascular biology 31, 624-633 (2011).

De Candia E, et al. Binding of thrombin to glycoprotein Ib accelerates the hydrolysis of Par-1 on intact platelets. J Biol Chem. 2001;276(7):4692-8.

De Meyer SF, et al. Platelet glycoprotein Ibalpha is an important mediator of ischemic stroke in mice. Exp Transl Stroke Med. 2011;3:9.

Denorme F, et al. Inhibition of Thrombin-Activatable Fibrinolysis Inhibitor and Plasminogen Activator Inhibitor-1 Reduces Ischemic Brain Damage in Mice. Stroke. 2016;47(9):2419-22.

Denorme F, et al. Platelet necrosis mediates ischemic stroke outcome in mice. Blood. 2020;135(6):429-40.

Denorme F, et al. The VWF-GPIb axis in ischaemic stroke: lessons from animal models. Thromb Haemost. 2016;116(4):597-604.

Deppermann C, et al. Platelet secretion is crucial to prevent bleeding in the ischemic brain but not in the inflamed skin or lung in mice. Blood. 2017;129(12):1702-6.

Derian CK, et al. Blockade of the thrombin receptor protease-activated receptor-1 with a small-molecule antagonist prevents thrombus formation and vascular occlusion in nonhuman primates. The Journal of pharmacology and experimental therapeutics. 2003;304(2):855-61.

Dhanesha N, et al. Endothelial Cell-Derived von Willebrand Factor Is the Major Determinant That Mediates von Willebrand Factor-Dependent Acute Ischemic Stroke by Promoting Postischemic Thrombo-Inflammation. Arteriosclerosis, thrombosis, and vascular biology. 2016;36(9):1829-37.

Dhanesha N, et al. Fn-EDA (Fibronectin Containing Extra Domain A) in the Plasma, but Not Endothelial Cells, Exacerbates Stroke Outcome by Promoting Thrombo-Inflammation. Stroke. 2019;50(5):1201-9.

Duvernay, M. et al. Protease-activated receptor (PAR) 1 and PAR4 differentially regulate factor V expression from human platelets. Mol Pharmacol 83, 781-792 (2013).

Mumaw MM, et al. Development and characterization of monoclonal antibodies against Protease Activated Receptor 4 (PAR4). Thromb Res. 2015;135(6):1165-71.

Murata T, et al. Altered pain perception and inflammatory response in mice lacking prostacyclin receptor. Nature. 1997;388(6643):678-82.

Murray R, et al. Prostaglandin endoperoxide/thromboxane A2 receptor desensitization. Cross-talk with adenylate cyclase in human platelets. J Biol Chem. 1990;265(35):21670-5.

Nakamura S, et al. Expandable megakaryocyte cell lines enable clinically applicable generation of platelets from human induced pluripotent stem cells. Cell Stem Cell. 2014;14(4):535-48.

Nakamura, N., et al. "Purification and characterization of a vimentin-specific protease in mouse myeloid leukemia cells: Regulation during differentiation and identity with cathepsin G." European journal of biochemistry 205.3 (1992): 947-954.

NERI Serneri GG, et al. Enhanced prostacyclin production by dipyridamole in man. Eur J Clin Pharmacol. 1981;21 (1):9-15.

Oldham WM, et al. How do receptors activate G proteins? Adv Protein Chem. 2007;74:67-93.

Palczewski K et al., Crystal structure of rhodopsin: A G protein-coupled receptor. Science 289, 739-745 (2000).

Pavic G et al., Thrombin receptor protease-activated receptor 4 is a key regulator of exaggerated intimal thickening in diabetes mellitus. Circulation 130, 1700-1711 (2014).

Pena-Martinez C, et al. Pharmacological Modulation of Neutrophil Extracellular Traps Reverses Thrombotic Stroke PA (Tissue-Type Plasminogen Activator) Resistance. Stroke. 2019;50(11):3228-37.

Pham, CTN. "Neutrophil serine proteases: specific regulators of inflammation." Nature Reviews Immunology 6.7 (2006): 541-550.

Polanowska J. et al., Specificity of human cathepsin G. Biochim Biophys Acta 1386, 189-198 (1998).

Prodan CI, et al. Higher coated-platelet levels are associated with stroke recurrence following nonlacunar brain infarction. J Cereb Blood Flow Metab. 2013;33(2):287-92.

Prodan CI, et al. Lower coated-platelet levels are associated with early hemorrhagic transformation in patients with non-lacunar brain infarction. Journal of thrombosis and haemostasis : JTH. 2010;8(6):1185-90.

Rajagopal S, et al. GPCR desensitization: Acute and prolonged phases. Cell Signal. 2018;41:9-16.

Rawlings ND, et al. The MEROPS database of proteolytic enzymes, their substrates and inhibitors in 2017 and a comparison with peptidases in the PANTHER database. Nucleic Acids Res. 2018;46(D1):D624-D32.

Raymond W.W. et al., How immune peptidases change specificity: cathepsin G gained tryptic function but lost efficiency during primate evolution. J Immunol 185, 5360-5368 (2010).

Rehault S. et al. New, sensitive fluorogenic substrates for human cathepsin G based on the sequence of serpin-reactive site loops. J Biol Chem 274, 13810-13817 (1999).

Renesto P. et al. Specific inhibition of thrombin-induced cell activation by the neutrophil proteinases elastase, cathepsin G, and proteinase 3: evidence for distinct cleavage sites within the aminoterminal domain of the thrombin receptor. Blood 89, 1944-1953 (1997).

(56) References Cited

OTHER PUBLICATIONS

Renesto, P. et al. Enhancement of cathepsin G-induced platelet activation by leukocyte elastase: consequence for the neutrophil-mediated platelet activation. Blood 82, 139-144 (1993).
Renesto, P. et al. Proteinase 3. A neutrophil proteinase with activity on platelets. J Immunol 152, 4612-4617 (1994).
Romson JL, Hook BG, Kunkel SL, Abrams GD, Schork MA, Lucchesi BR. Reduction of the extent of ischemic myocardial injury by neutrophil depletion in the dog. Circulation. 1983;67(5):1016-23.
Rossaint, J. et al. Role of Platelets in Leukocyte Recruitment and Resolution of Inflammation. Front Immunol 9, 2712 (2018).
Sacco RL, et al. Stroke incidence among white, black, and Hispanic residents of an urban community: the Northern Manhattan Stroke Study. Am J Epidemiol. 1998;147(3):259-68.
Sambrano, G. R., et al. "Cathepsin G activates protease-activated receptor-4 in human platelets." Journal of Biological Chemistry 275.10 (2000): 6819-6823.
Sambrano, G.R. et al., Role of thrombin signalling in platelets in haemostasis and thrombosis. Nature 413, 74-78 (2001).
Sasaki Y, Takahashi T, Tanaka I, Nakamura K, Okuno Y, Nakagawa O, Narumiya S, Nakao K. Expression of prostacyclin receptor in human megakaryocytes. Blood. 1997;90(3):1039-46.
Schmid DI, et al. Translational control of JunB, an AP-1 transcription factor, in activated human endothelial cells. J Cell Biochem. 2013;114(7):1519-28.
Seale, J., et al. "All-trans retinoic acid rapidly decreases cathepsin G synthesis and mRNA expression in acute promyelocytic leukemia." Leukemia 10.1 (1996): 95-101.
Belak, M. A. et al. Cathepsin G is a strong platelet agonist released by neutrophils. Biochem J 251, 293-299 (1988).
Senchenkova EY, et al. Novel Role for the AnxA1-Fpr2/ALX Signaling Axis as a Key Regulator of Platelet Function to Promote Resolution of Inflammation. Circulation. 2019;140(4):319-35.
Seshadri S, et al. Parental occurrence of stroke and risk of stroke in their children: the Framingham study. Circulation. 2010;121(11):1304-12.
Shakil H, et al. Genetic Deletion of Prostacyclin IP Receptor Exacerbates Transient Global Cerebral Ischemia in Aging Mice. Brain Sci. 2013;3(3):1095-108.
Shapiro MJ, et al. Role of the thrombin receptor's cytoplasmic tail in intracellular trafficking. Distinct determinants for agonist-triggered versus tonic internalization and intracellular localization. J Biol Chem. 1996;271(51):32874-80.
Shimoda N, et al. Cathepsin g is required for sustained inflammation and tissue injury after reperfusion of ischemic kidneys. Am J Pathol. 2007;170(3):930-40.
Sidhu, T.S. et al. Differential signaling by protease-activated receptors: implications for therapeutic targeting. Int J Mol Sci 15, 6169-6183 (2014).
Simon LM, et al. Human platelet microRNA-mRNA networks associated with age and gender revealed by integrated plateletomics. Blood. 2014;123(16):e37-45.
Simon LM, et al. Integrative Multi-omic Analysis of Human Platelet eQTLs Reveals Alternative Start Site in Mitofusin 2. Am J Hum Genet. 2016;98(5):883-97.
Smith TH, et al. Protease-activated Receptor-4 Signaling and Trafficking Is Regulated by the Clathrin Adaptor Protein Complex-2 Independent of beta-Arrestins. J Biol Chem. 2016;291(35):18453-64.
Smyth EM, Austin SC, Reilly MP, FitzGerald GA. Internalization and sequestration of the human prostacyclin receptor. J Biol Chem. 2000;275(41):32037-45.
Soh UJ, et al. Signal transduction by protease-activated receptors. Br J Pharmacol. 2010;160(2):191-203.
Spronk HMH, et al. Atherothrombosis and Thromboembolism: Position Paper from the Second Maastricht Consensus Conference on Thrombosis. Thromb Haemost. 2018;118(2):229-50.
Stefanini L, et al. RASA3 is a critical inhibitor of RAP1-dependent platelet activation. J Clin Invest. 2015: 1419-1432.
Stegner D, et al. Pharmacological inhibition of phospholipase D protects mice from occlusive thrombus formation and ischemic stroke-brief report. Arteriosclerosis, thrombosis, and vascular biology. 2013;33(9):2212-7.
Stitham J, et al. Clusters of transmembrane residues are critical for human prostacyclin receptor activation. Biochemistry. 2004;43(28):8974-86.
Stoller, M. L., et al. "Cathepsin G Cleavage of PAR4 Generates a Novel Tethered Ligand That Induces Platelet Activation." Blood 136 (2020): 2.
Sumbria RK, et al. Effects of phosphodiesterase 3A modulation on murine cerebral microhemorrhages. J Neuroinflammation. 2017;14(1):114.
Takahashi T. et al., Relation between neutrophil counts on admission, microvascular injury, and left ventricular functional recovery in patients with an anterior wall first acute myocardial infarction treated with primary coronary angioplasty. The American journal of cardiology 100, 35-40 (2007).
Tamura A, et al. Focal cerebral ischaemia in the rat: 1. Description of technique and early neuropathological consequences following middle cerebral artery occlusion. J Cereb Blood Flow Metab. 1981;1(1):53-60.
Temple K.J. et al., Development of a Series of (1-Benzyl-3-(6-methoxypyrimidin-3-yl)-5-(trifluoromethoxy)-1H-Indol-2-yl)methanol s as Selective Protease Activated Receptor 4 (PAR4) Antagonists with in Vivo Utility and Activity Against gamma-Thrombin. J Med Chem 59, 7690-7695 (2016).
Wagenblast E, et al. Functional profiling of single CRISPR/Cas9-edited human long-term hematopoietic stem cells. Nat Commun. 2019; 10(1):4730.
Zhang, M., et al. "A Novel HLA-A* 0201 Restricted Peptide Derived from Cathepsin G Is an Effective Immunotherapeutic Target in Acute Myeloid LeukemiaCathepsin G Is a Novel Target in Myeloid Leukemia." Clinical Cancer Research 19.1 (2013):247-257.
Zhou P, et al. Interactions between neutrophil extracellular traps and activated platelets enhance procoagulant activity In acute stroke patients with ICA occlusion. EBioMedicine. 2020;53:102671.

* cited by examiner

FIG. 2E

SEQ ID NO: 1

36-DDSTPSILPAPRGYPGQVCANDSDTLELPDSSRALLGWVPTR-78

| PAR4-B | PAR4-C |
|---|---|
| SEQ ID NO: 7 | SEQ ID NO: 8 |

FIG. 2F

Experimental spectrum showing peaks at 588.33, 589.09, 593.16, 593.33 across m/z 588–594.

PAR4-C No CatG chromatogram showing peaks at 32.84, 36.40, 54.31, 54.37 (PAR4-C) across Time (min) 20–70.

PAR4  36-DDSTPSILPAPRGYPGQVCANDSDTLELPDSSRALLLGWVPTR-78  SEQ ID NO: 1

PAR4-B  SEQ ID NO: 7

PAR4-C  SEQ ID NO: 8

| | | |
|---|---|---|
| Human | -SRALLLGWVPTR- | SEQ ID NO: 11 |
| Dog | -SRALLLGWVATR- | SEQ ID NO: 12 |
| Mouse | -SQALLLGWVPTR- | SEQ ID NO: 13 |
| Rat | -SEALLLGWVPTR- | SEQ ID NO: 14 |

FUNCTIONAL AND THERAPEUTIC EFFECTS OF PAR4 CLEAVAGE BY CATHEPSIN G

CROSS-REFERENCE TO RELATED APPLICATIONS

This application claims priority to U.S. Provisional Patent Application No. 63/247,636, filed Sep. 23, 2021, which is incorporated herein by reference in its entirety.

STATEMENT REGARDING FEDERALLY SPONSORED RESEARCH

This invention was made with government support under grant HL160808 awarded by the National Institutes of Health. The government has certain rights in the invention.

REFERENCE TO SEQUENCE LISTING

This application was filed with a Sequence Listing XML in ST.26 XML format in accordance with 37 C.F.R. § 1.821. The Sequence Listing XML file submitted in the USPTO Patent Center, "026389-9327-US02-REPLACEMENT-SE-QUENCE-LISTING.xml," was created on Dec. 12, 2022, contains 28 sequences, has a file size of 27.2 Kbytes, and is incorporated by reference in its entirety into the specification.

FIELD

This disclosure relates to a synthetic peptide mimetic and compositions comprising the synthetic peptide mimetic that induce activation of and signaling through PAR4. The disclosure further relates to methods of treating a bleeding disorder comprising administering the synthetic peptide.

INTRODUCTION

Human platelets express two G-protein coupled, protease-activated receptors (PAR1 and PAR4). Although many serine proteases activate platelets through PARs, thrombin is the best studied. PARs are activated by proteolysis of their amino termini. The resulting new N-terminus functions as a tethered ligand that binds to an extracellular loop of the PAR, resulting in platelet activation. Compared with PAR1, PAR4 has been less studied, but recent findings emphasize its importance and potential as a therapeutic target. PAR1 has a higher affinity for thrombin, and $Ca^{2+}$ transients rise and fall sharply after activation. In contrast, PAR4 acts as an "amplifier," inducing a gradual but sustained rise in $Ca^{2+}$ that accounts for greater intracellular $Ca^{2+}$ flux, thrombin generation, and fibrin formation under shear stress.

Elevated blood neutrophil levels correlate with ischemic arterial events, and platelet-leukocyte aggregates are elevated during a stroke. Activated neutrophils release the serine protease cathepsin G (CatG) at sites of injury and inflammation. CatG is a potent human PAR4-dependent platelet agonist, but it is unknown where CatG cleaves PAR4 and how this cleavage might activate the receptor.

Thus, there is a need for a synthetic peptide that activates PAR4 and induces platelet activation, granule release, and aggregation as a therapeutic.

SUMMARY

In an aspect, the disclosure relates to a synthetic peptide mimetic comprising an amino acid sequence of SEQ ID NO: 1. In an embodiment, the synthetic peptide mimetic induces activation of and signaling through PAR4. In another embodiment, the synthetic peptide mimetic induces PAR4-dependent calcium flux. In another embodiment, the synthetic peptide mimetic induces platelet aggregation. In another embodiment, the synthetic peptide mimetic induces platelet activation.

In a further aspect, the disclosure relates to a composition comprising the synthetic peptide mimetic of as described herein. In an embodiment, the composition further comprises a pharmaceutically acceptable carrier.

Another aspect of the disclosure provides a method of treating a bleeding disorder, the method comprising administering to a subject a therapeutically effective amount of a synthetic peptide mimetic comprising an amino acid sequence of SEQ ID NO: 1. In an embodiment, the synthetic peptide mimetic induces activation of and signaling through PAR4 in the subject. In another embodiment, the synthetic peptide mimetic induces PAR4-dependent calcium flux in the subject. In another embodiment, the synthetic peptide mimetic induces platelet aggregation in the subject. In another embodiment, the synthetic peptide mimetic induces platelet activation in the subject. In another embodiment, the bleeding disorder is hemophilia A (factor VIII deficiency), hemophilia B (factor IX deficiency), von Willebrand disease, thrombocytopenia, or bleeding due to qualitative platelet dysfunction. In another embodiment, the bleeding disorder is a result caused by cirrhosis of the liver, leukemia, vitamin K deficiency, administration of aspirin, administration of heparin, or administration of warfarin.

The disclosure provides for other aspects and embodiments that will be apparent in light of the following detailed description and accompanying figures.

BRIEF DESCRIPTION OF THE DRAWINGS

FIG. 1A is a bar chart showing activation of washed platelets (n=4) that were treated with varying concentrations of cathepsin G (CatG), elastase, or proteinase 3 (PR3). Platelet activation was measured by PAC-1 binding (mean %+SEM). FIG. 1B is a graph showing representative tracing of washed platelets treated with 400 nM cathepsin G, elastase, or proteinase 3. FIG. 1C is a bar chart showing platelet aggregation data displayed as mean maximum (max)+SEM; n=3 independent experiments. P<0.001 indicates the differences between CatG and the other groups (elastase or proteinase 3). FIG. 1D is a bar chart showing activation of washed platelets (Plts) and neutrophils (PMNs) from healthy donors (n=14) that were suspended in the presence or absence of the neutrophil activating agonist N-formyl-methionyl-leucyl-phenylalanine (fMLP, 10 UM), cytochalasin B (CyB, 5 μg/mL), and/or cathepsin G inhibitor (CatG Inh), 1 μM). Platelet activation was measured by PAC-1 binding and displayed as mean fluorescence intensity (MFI; mean+SEM).

FIGS. 2A-2I show that neutrophil cathepsin G cleaves PAR4 at $Ser^{67}$-$Arg^{68}$ to induce platelet aggregation. FIG. 2A is a bar chart showing the maximum platelet aggregation (percent +SEM) of washed platelets that were treated with varying concentrations of CatG in the presence or absence of the PAR4 inhibitor, BMS-986120 (400 nM BMS; n=5). The PAR1 activation peptide (SFLLRN (SEQ ID NO: 28); 10 μM) served as a negative control (n=5) for PAR4 inhibition. FIG. 2B is a graph showing platelet activation (measured by PAC-1 binding (Ala: n=7; Thr: n=7) and displayed as MFI (mean+SEM) of washed platelets that were stimulated with increasing concentrations of CatG. FIG. 2C is a schematic showing the PAR4 amino acid sequence targeted by RC3 monoclonal antibody (SEQ ID NO: 6), and a graph showing aggregation of platelets treated with thrombin or 200 nM CatG in the presence or absence of RC3. In the schematic, the underlined amino acids in the sequence represent the tethered ligand generated by thrombin, and the arrow represents the location of the canonical thrombin cleavage site. The aggregation studies depicted in the graph were performed with PAR1 blockade using 100 nM vorapaxar, with representative tracing of washed platelets treated with 0.25 U/mL thrombin or 200 nM CatG in the presence or absence of RC3. FIG. 2D is a bar chart showing quantification of maximum (max) platelet aggregation (mean percent+SEM) (n=3 different subjects). FIG. 2E is a schematic showing PAR4-B (SEQ ID NO: 7) and PAR4-C (SEQ ID NO: 8) peptide sequences used in CatG proteolysis analysis by LC-MS/MS. The grey sequence indicates the novel tethered ligand generated by CatG (SEQ ID NO: 1). FIG. 2F is a pair of spectra showing the results of LC-MS/MS performed on PAR4-C in the absence of CatG. Time of flight analysis showed an experimental peak with the correct mass (m) over charge (z) ratio. FIG. 2G is a series of spectra showing the results of LC-MS/MS analysis performed on PAR4-C after incubation with 400 nM CatG at 37°C for 15 minutes, and the expected m/z ratio of DSDTLELPSS (SEQ ID NO: 9) shown below the experimental graph for reference. Time of flight analysis observed a peak with the correct m/z ratio of a fragment containing the amino acids DSDTLELPSS (SEQ ID NO: 9) (the last residue is Ser67), indicating CatG cleaved PAR4-C between $Ser^{67}$ and $Arg^{68}$. FIG. 2H is a graph showing calcium mobilization of WT, mutated PAR4, or empty vector (mock) that were expressed in HEK293T/17 cells treated with or without CatG (2.5 µM) in the presence of PAR1 blockade with 100 nM vorapaxar. FIG. 2I is a graph showing calcium mobilization of WT, mutated PAR4, or empty vector (mock) that were expressed in HEK293T/17 cells and treated with thrombin (1.5 U/mL) in the presence of 100 nM vorapaxar. Solid thick lines and thin vertical lines are means and SEMs, respectively. n=4 independent experiments performed in duplicate in FIGS. 2H-I.

FIG. 6A is a schematic showing PAR4-B (SEQ ID NO: 7) and PAR4-C (SEQ ID NO: 8) peptide sequences used in mass spectrometry analysis to determine thrombin and cathepsin G cleavage sites. The grey sequence indicates the tethered ligand generated by CatG. FIG. 6B is a series of spectra showing results from Orbitrap liquid chromatography-mass spectrometry (LC-MS/MS) that was performed on PAR4-B in the absence or presence of thrombin (100 U/mL) or cathepsin G (400 nM). Thrombin proteolyzed virtually all of the PAR4-B peptide, whereas CatG left the PAR4-B peptide largely intact.

FIG. 7A is a graph showing calcium mobilization for WT human PAR4 (hPAR4) or empty vector (mock) that was expressed in HEK293T/17 cells and treated with 1.5 mM RALLLGWVPTR (SEQ ID NO: 1) (RA-11mer, solid line) or tyrodes (dash lines). Thick lines and thin vertical lines are means and SEMs, respectively. n=3 independent experiments performed in duplicate. FIGS. 7B and 7C are bar charts showing platelet activation for washed platelets (n=6) that were treated with buffer or 1 mM RA-11mer having the amino acid sequence of SEQ ID NO: 1, where platelet activation was measured by (FIG. 7B) PAC-1 binding (mean percent+SEM) and (FIG. 7C) P-selectin expression (mean percent+SEM). FIG. 7D is a graph showing representative aggregation tracing of washed platelets treated with 1 mM GYPGQV (SEQ ID NO: 5) (GYP), ALLLGWVPTR (SEQ ID NO: 2) (AL-10mer), or RA-11mer having the amino acid sequence of SEQ ID NO: 1.

FIG. 7E is a bar chart showing maximum (max) aggregation of platelets treated with buffer or 1 mM of each indicated peptide (mean percent+SEM; n=5). FIG. 7F is a graph showing representative tracing of platelet calcium flux induced by RA-11mer having the amino acid sequence of SEQ ID NO: 1 (2 mM). Tyrodes buffer served as a negative control. n=4 independent experiments performed in duplicate. FIG. 7G is a graph showing representative tracing of washed platelets treated with 1 mM or 10 mM RA-6mer having the amino acid sequence of SEQ ID NO: 4 or 1 mM RA-11mer having the amino acid sequence of SEQ ID NO: 1. FIG. 7H is a bar chart showing quantification of maximum (max) aggregation (percent+SEM) elicited by treatment of same subjects' platelets with RA-11mer having the amino acid sequence of SEQ ID NO: 1 or RA-6mer having the amino acid sequence of SEQ ID NO: 4 (1 mM, n=3). FIG. 7I is a schematic showing dog (SEQ ID NO: 12), human (SEQ ID NO: 11), mouse (SEQ ID NO: 13), and rat (SEQ ID NO: 14) PAR4 sequence alignment of the 12 amino acids adjacent to the plasma membrane of the first (N-terminal) PAR4 extracellular domain. Arrow indicates $Arg^{68}$ in humans where CatG cleaves PAR4. FIGS. 7J-7L are graphs showing representative aggregation tracing of dog, human, mouse, and rat washed platelets treated with 1 U/mL human thrombin (FIG. 7J), 1 µM human CatG (FIG. 7K), or 1 mM RA-11mer having the amino acid sequence of SEQ ID NO: 1 (FIG. 7L). n >3 for human and mouse (FIGS. 7J-7L); n=2 for dog and rat (FIGS. 7J-7K); n=2 for rat (FIG. 7L); n=1 for dog (FIG. 7L).

DETAILED DESCRIPTION

Figure 1A:
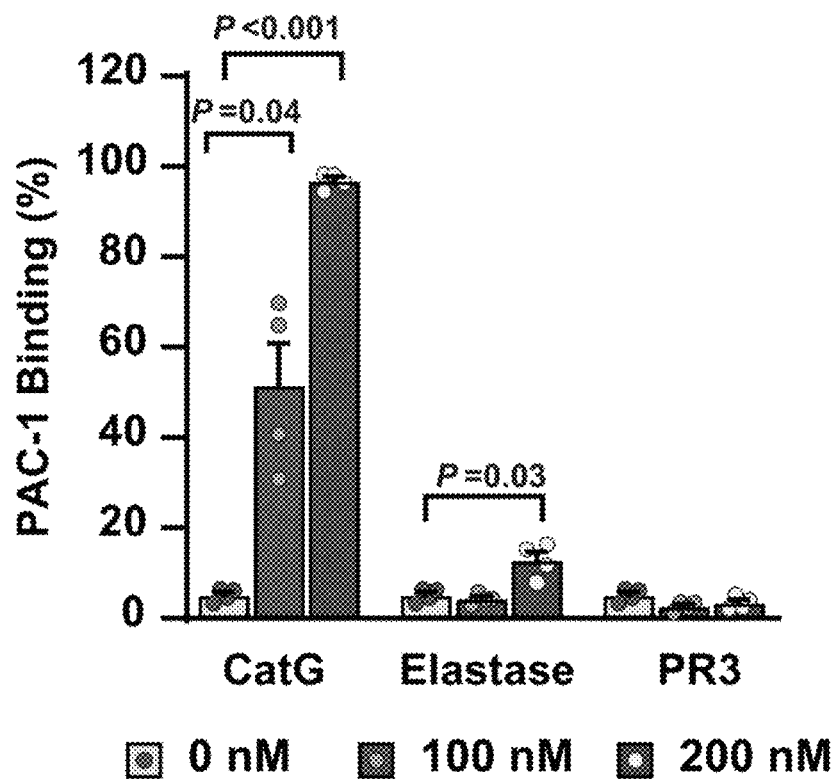
FIGS. 1A-1D shows that platelet aggregation is induced by different neutrophil proteases.
Figure 1B:
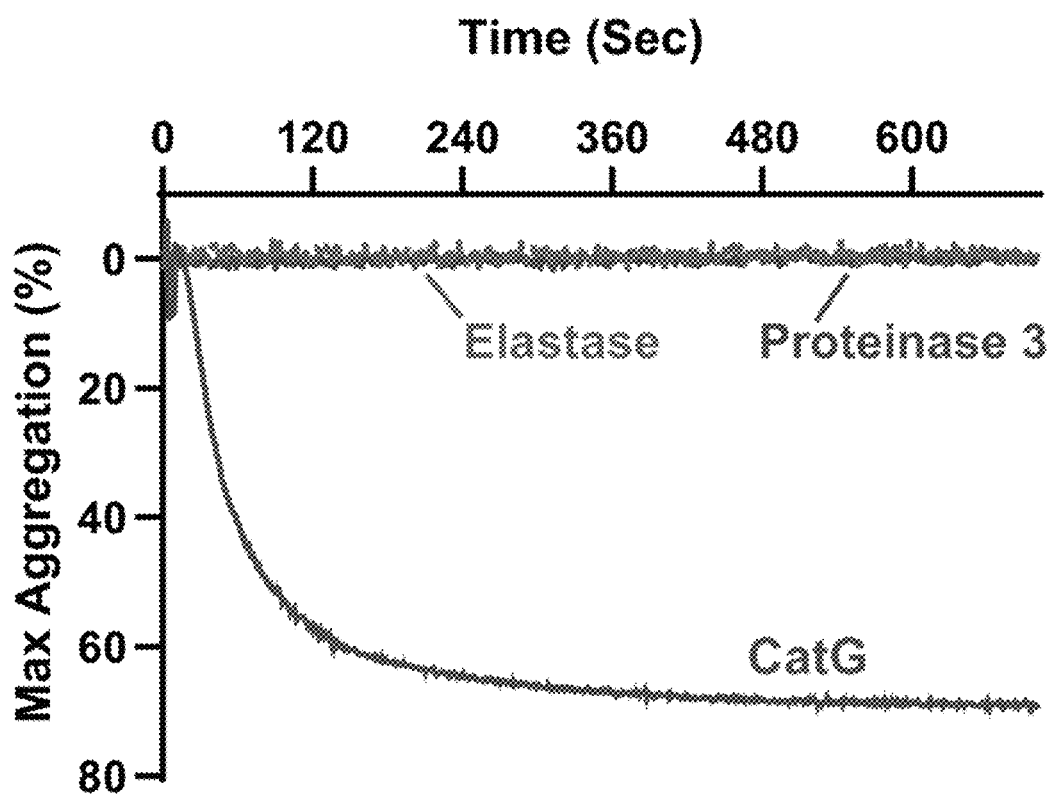
Figure 1C:
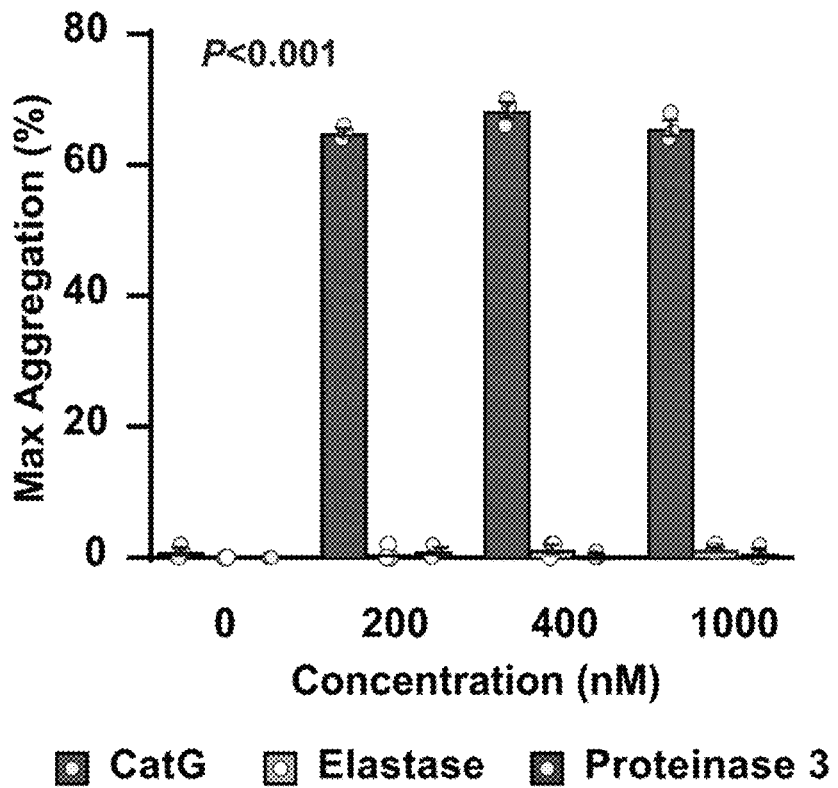
Figure 1D:
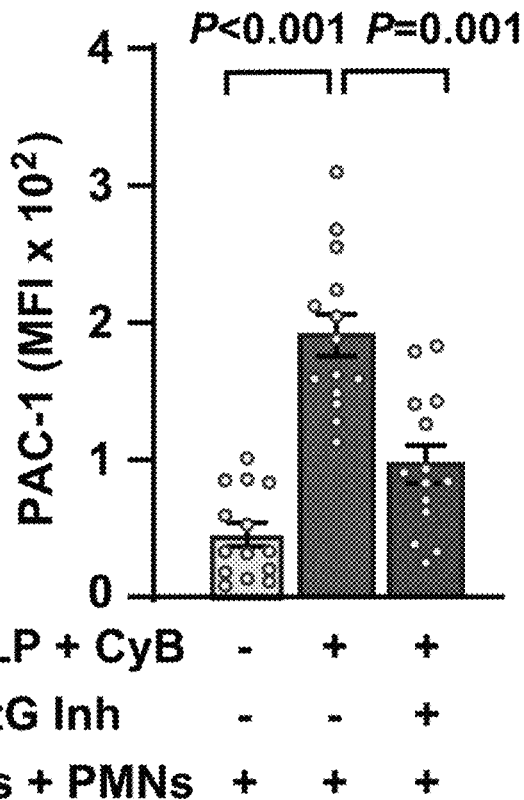

Described herein are a synthetic peptide mimetic and compositions comprising the synthetic peptide mimetic that induce activation of and signaling through PAR4. Also described herein are methods of treating a bleeding disorder comprising administering the synthetic peptide.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Binding region" as used herein refers to the region within a target region that is recognized and bound by the synthetic peptide mimetic.

As used herein, "bleeding disorder" refers to a group of conditions in which there is a problem with the body's blood clotting process. These disorders can lead to heavy and prolonged bleeding after an injury. Bleeding can also begin on its own.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

The terms "control," "reference level," and "reference" are used herein interchangeably. The reference level may be a predetermined value or range, which is employed as a benchmark against which to assess the measured result. "Control group" as used herein refers to a group of control subjects or cells. A control may be a subject or cell without a synthetic peptide mimetic as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

"Nucleic acid" or "oligonucleotide" or "polynucleotide" as used herein means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a target sequence under stringent hybridization conditions. Thus, a polynucleotide also encompasses a probe that hybridizes under stringent hybridization conditions. Polynucleotides may be single stranded or double stranded or may contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

The term "PAR4 agonist peptide" as used herein refers to a peptide that can fully or partially activate the PAR4 receptor and elicit signaling events and or functional responses associated with PAR4 receptor activation. A PAR4 agonist peptide may be a synthetic peptide mimetic as described herein.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, for example, enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. A motif may include 3, 4, 5, 6, or 7 sequential amino acids. A domain may be comprised of a series of the same type of motif.

The term "recombinant" when used with reference to, for example, a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed, or not expressed at all.

"Sample" or "test sample" as used herein can mean any sample in which the presence and/or level of a target is to be detected or determined or any sample comprising a synthetic peptide mimetic or component thereof as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" and "patient" as used herein interchangeably refers to any vertebrate, including, but not limited to, a mammal that wants or is in need of the herein described compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgous monkey, rhesus monkey, chimpanzee, gorilla, orangutan, and gibbon. The subject may be of any age or stage of development, such as, for example, an adult, an adolescent, or an infant. The subject may be male. The subject may be female. In some embodiments, the subject has a specific genetic marker. The subject may be undergoing other forms of treatment.

"Synthetic peptide" as used herein refers to chemically synthesized small polymers of amino acids. For example, a synthesis reaction to produce a synthetic peptide may consist of joining the carboxyl group of an amino acid to the amino group of the previous amino acid in the peptide chain. Various reactive groups on the side chains and termini may be chemically protected to prevent undesired reactions from occurring.

"Target region" as used herein refers to the region of the target receptor to which the synthetic peptide mimetic is designed to bind.

"Treatment" or "treating" or "treatment" when referring to protection of a subject from a disease, means suppressing, repressing, reversing, alleviating, ameliorating, or inhibiting the progress of disease, or completely eliminating a disease. A treatment may be either performed in an acute or chronic way. The term also refers to reducing the severity of a disease or symptoms associated with such disease prior to affliction with the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. Representative examples of "biological activity" include the ability to be bound by a specific antibody or polypeptide or to promote a clotting response. Variant can mean a functional fragment thereof. Variant can also mean multiple copies of a polypeptide. The multiple copies can be in tandem or separated by a linker. A conservative substitution of an amino acid, for example, replacing an amino acid with a different amino acid of similar properties (for example, hydrophilicity, degree and distribution of charged regions) is recognized in the art as typically involving a minor change. These minor changes may be identified, in part, by considering the hydropathic index of amino acids, as understood in the art (Kyte et al., J. Mol. Biol. 1982, 157, 105-132). The hydropathic index of an amino acid is based on a consideration of its hydrophobicity and charge. It is known in the art that amino acids of similar hydropathic indexes may be substituted and still retain protein function. In one aspect, amino acids having hydropathic indexes of +2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Synthetic Peptide Mimetic

Provided herein are synthetic peptide mimetics. The synthetic peptide mimetic may induce activation of and signaling through Protease-Activated Receptor 4 (PAR4). PARs are integral membrane proteins that are coupled to G-proteins and are activated by specific cleavage of the amino terminal (N-terminal) sequence that exposes a new N-terminal sequence that functions as a tethered ligand, which binds a conserved region on extracellular loop 2 (ECL2) of a PAR. This binding causes a specific conformational change in the PAR and alters the affinity for an intracellular G-protein. PARs can act through G-proteins i (CAMP inhibitory), 12/13 (Rho and Ras activation), and q (calcium signalling). Four types of PARs have been identified and it has been shown that a large group of proteases cleave and activate PARs, including various endogenous proteases such as proteases involved in the coagulation cascade, inflammatory cells, and the digestive tract. In particular, PARs may be activated by serine proteases such as thrombin that acts on PARs 1, 3, and 4, and trypsin that acts on PAR2. PARs can also be specifically cleaved and irreversibly activated by exogenous proteases originated from insects, bacteria, plants, and fungi. An embodiment of the present disclosure provides an 11mer PAR4 agonist peptide or synthetic peptide mimetic (SEQ ID NO: 1) having improvement in potency relative to 10-mer (SEQ ID NO: 2), 8-mer (SEQ ID NO: 3), and two 6-mer (SEQ ID NOs: 4 and 5) agonist peptides or synthetic peptide mimetics.

The synthetic peptide mimetic disclosed herein may have an amino acid sequence comprising SEQ ID NO: 1. The synthetic peptide mimetic disclosed herein may have the amino acid sequence of SEQ ID NO: 1. The synthetic peptide mimetic disclosed herein may have an amino acid sequence that is a variant of SEQ ID NO: 1 but that retains the biological function of a peptide having the amino acid sequence of SEQ ID NO: 1. For example, the synthetic peptide mimetic may have a sequence with greater than 80% homology to SEQ ID NO: 1, such as a sequence with greater than 90% homology to SEQ ID NO:1, while still retaining the biological function of the peptide having the amino acid sequence of SEQ ID NO: 1. The synthetic peptide mimetic disclosed herein may be used as an agonist to activate PAR4. The synthetic peptide mimetic described herein may induce PAR4-dependent calcium flux. The synthetic peptide mimetic described herein may induce platelet aggregation, platelet activation, or a combination thereof.

The syntheses of the synthetic peptide mimetics described herein can be carried out by any method known in the art. For example, the peptides described herein may be produced by chemical synthesis using various solid-phase techniques such as those described in Barany et al., The Peptides: Analysis, Synthesis, Biology, Volume 2: "Special Methods in Peptide Synthesis, Part A", pp. 3-284, Gross et al., eds., Academic Press, New York, publ. (1980); and in Stewart et al., Solid-Phase Peptide Synthesis, 2nd Edition, Pierce Chemical Co., Rockford, Ill., publ. (1984). The peptide synthesis may be based on the Fmoc (9-Fluorenylmethyl methyl-oxycarbonyl) group for temporary protection of the α-amino group, in combination with the tert-butyl group for temporary protection of the amino acid side chains (see, for example, Atherton et al., "The Fluorenylmethoxycarbonyl Amino Protecting Group", in The Peptides: Analysis, Synthesis, Biology, Volume 9: "Special Methods in Peptide Synthesis, Part C", pp. 1-38, Undenfriend, S. et al., eds., Academic Press, San Diego, publ. (1987).

In some embodiments, the peptides can be synthesized in a stepwise manner on an insoluble polymer support (also referred to as "resin") starting from the C-terminus of the peptide. A synthesis may be begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) and, after completion of the peptide sequence assembly, the resulting peptide alcohol may be released with LiBH4 in THF (see Stewart et al., supra, p. 92).

The peptide mimetic may also be synthesized by recombinant methods where the peptide may be produced through recombinant DNA technology. This may involve inserting DNA encoding the peptide into bacterial or mammalian cells, expressing the peptide in the cells, and then purifying the peptide mimetic from the cells using methods known in the art.

3. Compositions

Further provided herein are compositions comprising the above-described peptide mimetics. In some embodiments, the composition may comprise from about 0.1 mM to about 30 mM, from about 1 mM to about 30 mM, from about 5 mM to about 30 mM, from about 10 mM to about 30 mM, from about 15 mM to about 30 mM, from about 20 mM to about 30 mM, from about 25 mM to about 30 mM, from about 0.1 mM to about 25 mM, from about 0.1 mM to about 20 mM, from about 0.1 mM to about 15 mM, from about 0.1 mM to about 10 mM, from about 0.1 mM to about 5 mM, or from about 0.1 mM to about 1 mM of the peptide mimetic. The peptide mimetics as detailed herein may be formulated into compositions in accordance with standard techniques well known to those skilled in the pharmaceutical art. The compositions can be formulated according to the mode of administration to be used. In cases where compositions are injectable compositions, the compositions may be sterile, pyrogen free, and particulate free. An isotonic formulation may also be used. Generally, additives for isotonicity may include sodium chloride, dextrose, mannitol, sorbitol, and lactose. In some cases, isotonic solutions such as phosphate buffered saline may be preferred. Stabilizers may include gelatin and albumin. In some embodiments, a vasoconstriction agent may be added to the formulation.

The composition may further comprise a pharmaceutically acceptable excipient. The pharmaceutically acceptable excipient may include functional molecules as vehicles, adjuvants, carriers, or diluents. The term "pharmaceutically acceptable carrier," may be a non-toxic, inert solid, semi-solid or liquid filler, diluent, encapsulating material, or formulation auxiliary of any type. Pharmaceutically acceptable carriers may include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof. The pharmaceutically acceptable excipient may be an electroporation or microinjection facilitating agent.

The composition may further comprise one or more additional therapeutic agent(s). The additional therapeutic agent(s) may be agent(s) that induce clotting or platelet aggregation such as clotting factor products, ACE 910 or emicizumab, desmopressin acetate, epsilon amino caproic acid, cryoprecipitate, and the like.

4. Administration

The peptide mimetics disclosed herein or compositions comprising the same may be administered or delivered to a cell. The cell may be a platelet. The cell may be in a subject. Methods of introducing a peptide into a host cell are known in the art, and any known method can be used to introduce a peptide into a cell. Suitable methods may include, for example, electroporation, direct micro injection, and the like. The peptide mimetic or composition comprising the same may be electroporated using BioRad Gene Pulser Xcell or Amaxa Nucleofector IIb devices or other electroporation device.

The peptide mimetics as detailed herein or the pharmaceutical compositions comprising the same may be administered to a subject. Such compositions can be administered in dosages and by techniques well known to those skilled in the medical arts taking into consideration such factors as the age, sex, weight, and condition of the particular subject, and the route of administration. The presently disclosed peptide mimetics or compositions comprising the same may be administered to a subject by different routes including orally, parenterally, sublingually, transdermally, rectally, transmucosally, topically, intranasal, intravaginal, via inhalation, via buccal administration, intrapleurally, intravenous, intraarterial, intraperitoneal, subcutaneous, intradermally, epidermally, intramuscular, intranasal, intrathecal, intracranial, intraarticular, or combinations thereof. In certain embodiments, the peptide mimetic or composition comprising the same may be administered to a subject intravenously. The peptide mimetics or compositions comprising the same may be delivered to a subject by several technologies including liposome mediated, nanoparticle facilitated, recombinant vectors such as recombinant lentivirus, recombinant adenovirus, and recombinant adenovirus associated virus. For veterinary use, the peptide mimetics or compositions comprising the same may be administered as a suitably acceptable formulation in accordance with normal veterinary practice. The veterinarian may readily determine the dosing regimen and route of administration that is most appropriate for a particular animal. The peptide mimetics or compositions comprising the same may be administered by traditional syringes, or other physical methods such as electroporation ("EP"), "hydrodynamic method", or ultrasound.

5. Methods a. Methods of Treating a Bleeding Disorder

Provided herein are methods of treating a bleeding disorder. The methods may include administering to a subject a therapeutically effective amount of a synthetic peptide mimetic as detailed herein or a composition comprising the same. After administration, the synthetic peptide mimetic may induce activation of and signaling through PAR4 in the subject. After administration, the synthetic peptide mimetic may induce PAR4-dependent calcium flux in the subject. After administration, the synthetic peptide mimetic may induce platelet aggregation in the subject. After administration, the synthetic peptide mimetic may induce platelet activation in the subject.

The bleeding disorder may be hemophilia A (factor VIII deficiency), hemophilia B (factor IX deficiency), von Willebrand disease, thrombocytopenia, or bleeding due to qualitative platelet dysfunction. The bleeding disorder may be a result caused by cirrhosis of the liver, leukemia, vitamin K deficiency, administration of aspirin, administration of heparin, or administration of warfarin.

b. Methods of Inducing Platelet Activation or Aggregation

Provided herein are methods of inducing platelet activation or aggregation. The methods may include administering to a cell or a subject a therapeutically effective amount of a synthetic peptide mimetic as detailed herein or a composition comprising the same.

6. EXAMPLES

The foregoing may be better understood by reference to the following examples, which are presented for purposes of illustration and are not intended to limit the scope of the invention. The present disclosure has multiple aspects and embodiments, illustrated by the appended non-limiting examples.

Example 1

Materials and Methods

Subject recruitment and genotyping. Venous blood was drawn into acid citrate dextrose (BD, Franklin Lakes, NY, USA) following written consent obtained with approval from the Institutional Review Board of the University of Utah (IRB 00095539). Healthy donors over the age of 18 were genotyped for rs773902 F2RL3 (Ala120Thr) using the TaqMan SNP Genotyping Assay (Life Technologies, Carlsbad, CA, USA). Donors were excluded based on the following criteria: pregnancy, diagnosed bleeding disorder, use of more than one prescription medication, or daily use of antiplatelet, anticoagulants, or non-steroidal anti-inflammatory (NSAID) medications. Prior to donation, donors must have abstained from any use of NSAIDs for greater than 72 hours. Samples were excluded from analysis if platelets failed to aggregate to arachidonic acid or blood displayed abnormal closure time to epinephrine/collagen cartridges (Siemens) while maintaining normal ADP/collagen closure (Siemens) time assessed using the PFA-100 (Siemens), suggesting use of NSAIDs prior to donation.

Animal studies. Mouse platelets were isolated as previously described from C57BL/6 mice (Denorme et al., Blood. 2020; 135(6):429-440). Dog platelets were isolated from whole blood drawn into ACD using a similar isolation procedure as for human platelets. All animal studies were approved by the University of Utah Institutional Animal Care and Use Committee (18-10012).

Platelet and neutrophil isolation. Platelets and neutrophils were isolated as previously described (Yost et al., J Clin Invest. 2016; 126(10):3783-3798). Platelet isolation from dogs, rats and mice was approved by the IACUC. Platelet activation and aggregation were performed as previously described (Manne et al., Blood. 2020; 136(11): 1317-1329).

Platelet isolation, aggregation, and activation. Human washed platelets were prepared and resuspended in Tyrode's Buffer at $2\times10^8$/mL as described (Edelstein et al., Nat Med. 2013; 19(12):1609-1616). For human and dog platelet comparisons, platelets were prepared using a modified human platelet protocol with final concentrations of 1 M PGE1 (Cayman Chemical, Ann Arbor, MI, USA) used during centrifugation steps. Centrifugations after Tyrode's washes was decreased to 1,250×g as described in Cremer et al., PLOS One. 2019; 14(11): e0224891. Platelet aggregation was measured under stirring conditions at 37° C. using a PAP-8E aggregometer after treatment with the following agonists: arachidonic acid (Bio/Data Corporation, Horsham, PA, USA), cathepsin G, elastase, proteinase 3 (Athens Research Group), α-thrombin (Sigma, St. Louis, MO, USA), PAR-1 peptide (SFLLRN) (GL Biochem, China). P-selectin and PAC-1 were measured as previously described (Yee et al., J Thromb Haemost. 2006; 4(9):2043-2050; Tourdot et al., Arterioscler Thromb Vasc Biol. 2014; 34(12):2644-2650).

Neutrophil-Platelet Activation Assays. Neutrophils were isolated from whole blood using positive selection with CD15 microbeads as previously described (Middleton et al., Blood. 2020; 136(10):1169-1179). Neutrophils were resuspended in PBS+10% BSA at $4\times10^6$ neutrophils/mL. Platelets from the same donor ($5\times10^7$/mL) were incubated with FITC conjugated PAC1 antibody for 10 mins at 37° C. prior to addition of neutrophils. Neutrophils were activated with 10 μm N-formylmethionine-leucyl-phenylalanine (fMLP) and 10 μg/mL cytochalasin B (Sigma, St. Louis, MO, USA) and incubated at 37° C. for 60 minutes followed by fixation with 4% paraformaldehyde. In some experiments, a specific CatG inhibitor (Cathepsin G Inhibitor I, Sigma, St. Louis, MO, USA) was added. Platelet activation was measured by flow cytometric analysis using the Cytoflex flow cytometer (Beckman Coulter, Pasadena, CA, USA).

Antagonist Studies. Washed platelets were incubated for 15 minutes at 37° C. with PAR-4 blocking antibody RC3 (100 μg/mL) (generous gift from Regeneron Pharmaceuticals; French et al., Blood Adv. 2018; 2(11): 1283-1293), PAR-1 inhibitor vorapaxar (100 nM), and/or PAR-4 inhibitor BMS-986120 (400 nM) (Cayman Chemical, Ann Arbor, MI, USA).

PAR4 calcium flux assays. PAR4-dependent calcium flux was measured using Fura2-QBT in platelets and HEK293T/17 cells with wild-type (WT) and mutant PAR4 (Tourdot et al., Arterioscler Thromb Vasc Biol. 2014; 34(12):2644-2650).

PAR4 mutant calcium flux assays. Using Quikchange Lightning Site-Directed mutagenesis (Agilent) per manufacturing instructions, pCMV-Flag-PAR4-S66E, pCMV-Flag-PAR4-S67E, and pCMV-Flag-PAR4-R68E were generated from mutation of pCMV-Flag-PAR4 and confirmed by sequencing (University of Utah DNA Sequencing Core). Prior to transfection, HEK293T/17 cells (ATCC CRL-11268) were seeded at $4.5\times10^4$/mL. The following day, cells were transfected with the plasmid of interest using Lipofectamine 2000 (Invitrogen, Carlsbad, CA, USA). Twenty-four hours after transfection, media was removed and replaced with Optimem w/Glutamax (Gibco, Carlsbad, CA, USA) containing vorapaxar (100 nM) (Cayman Chemical, Ann Arbor, MI, USA) and Fura2-QBT (Molecular Devices). Following incubation for 1 hour at 37° C., plate was placed in the Flexstation 3 (Molecular Devices) where agonists, Tyrode's Buffer, cathepsin G (2.5 μM), or α-thrombin (1.5 U/mL), were injected onto cells and calcium mobilization was monitored and recorded.

Platelet calcium flux assay. Washed platelets were incubated at 37° C. for 1 hour in Tyrode's buffer (supplemented with pgel and heparin) with Fura-2AM (final concentration 2 μM). Platelets were washed and resuspended to a final concentration of $4\times10^8$/mL. Platelets were dispensed into a Costar 96-well half area clear bottom plate and placed in the Flexstation 3 (Molecular Devices) where cathepsin G (500 nM), buffer, or peptides (2 mM) were injected onto cells and calcium flux monitored.

PAR-4 Peptide and Cleavage Analysis. PAR4 synthetic peptides were incubated with protease, snapped frozen, and sent for mass spectrometry analysis. PAR-4B (DDSTPSIL-PAPRGYPGQVCANDS; SEQ ID NO: 7) and PAR-4C (DSDTLELPDSSRALLLGWVPTR; SEQ ID NO: 8) were synthesized by BIOMATIK (Wilmington, DE, USA). PAR4-B and PAR4-C were incubated with vehicle, thrombin (100 nM) or cathepsin G (400 nM) at 37° C. for 15 minutes to an hour depending on the experimental condition. After digestion with the indicated protease, reactions were snapped frozen and sent to the University of Arizona, Analytical and Biological Mass Spectrometry Core Facility (Tucson, Arizona) for analysis. LC-MS/MS analysis was done on a Q Exactive Plus mass spectrometer (Thermo Fisher Scientific, San Jose, CA) equipped with an EASY-Spray nanoESI source. Peptides (500 ng) were injected onto an Acclaim Pepmap 100 trap column (75 micron ID x 2 cm, Thermo Scientific), washed for 10 min at 3% mobile phase B (acetonitrile, 0.1% formic acid, mobile phase A consisting of water and 0.1% formic acid) then eluted onto an Acclaim PepMap RSLC analytical column (75 micron ID x 25 cm, Thermo Scientific using a 3-20% gradient of B over 40 min, 20-50% solvent B over 5 min, 50-95% of solvent B over 5 min, then a hold of solvent 95% B for 10 min, and finally a return to 3% solvent B for 1 min, then a hold at 3% B for 10 min. Flow rates were 300 nL/min using a Dionex Ultimate 3000 RSLCnano System (Thermo Scientific). Data dependent scanning was performed by the Xcalibur v 4.1.31.9 software (Andon et al., Proteomics. 2002; 2(9): 1156-1168) using a survey scan at 70,000 resolution scanning mass/charge (m/z) 350-1600 at an automatic gain control (AGC) target of 1e6 and a maximum injection time (IT) of 65 msec, followed by higher-energy collisional dissociation (HCD) tandem mass spectrometry (MS/MS) at 27nce (normalized collision energy), of the 11 most intense ions at a resolution of 17,500, an isolation width of 1.5 m/z, an AGC of 1e5 and a maximum IT of 65 msec. Dynamic exclusion was set to place any selected m/z on an exclusion list for 30 seconds after a single MS/MS. Ions of charge state+7, 8, >8, unassigned, and isotopes were excluded from MS/MS. MS and MS/MS data were searched against the N-terminal amidated PAR4 sequence using Proteome Discoverer v. 2.4.0.305 (Thermo Scientific). The peptide identification results were further analyzed with Scaffold Q+S v 4.8.7 (Proteome Software Inc., Portland OR), a program that relies on various search engine results (i.e.: Sequest, X!Tandem, MASCOT) and which uses Bayesian statistics to reliably identify more spectra9.

GYPGQV-NH2 (SEQ ID NO: 5), RALLLGWVPTR-NH2 (SEQ ID NO: 1), ALLLGWVPTR-NH2 (SEQ ID NO: 2), RALLLG-NH2 (SEQ ID NO: 4). Peptides were synthesized by BIOMATIK (Wilmington, DE, USA) at similar purities. All peptides were suspended in 50% DMSO and 50% ethanol. To measure platelet activation, washed platelets were stimulated with various concentrations of the peptide in the presence of CD41-APC, P-selectin (PE) and PAC-1 (FITC) for 15 minutes at 37° C. and then fixed with FACS Lysis Buffer. Samples were immediately run on a Cytoflex flow cytometer. In some experiments, platelets were stimulated with peptides and platelet aggregation performed as described above. Platelet calcium flux was induced by RALLLGWVPTR (2 mM; SEQ ID NO: 1), CatG (500 nM), ALLLGWVPTR (2 mM; SEQ ID NO: 2) or tyrodes buffer and monitored as described above.

Statistical Analysis. All statistical analyses were performed using GraphPad Prism (v9.0.0; San Diego, CA). Data comparison of two normally distributed groups was conducted using a two-tailed Student's or paired t-test. Comparison of three or more normally distributed groups with equal variances was done using a repeated measures or independent one-way analysis of variance with post-hoc Tukey's or Bonferroni's multiple comparisons test. Brown-Forsythe and Welch ANOVA test with post-hoc Dunnett's T3 multiple comparisons test was used for comparisons of groups with unequal variances. Comparison of two or more normally distributed groups under the influence of two independent variables was assessed using repeated measures, mixed effects, or independent two-way analysis of variance with post-hoc Bonferroni's multiple comparisons test. A P-value of <. 05 was considered statistically significant.

Example 2

CatG Elicits Platelet Activation and Aggregation Through PAR4 Signaling

Figure 2A:
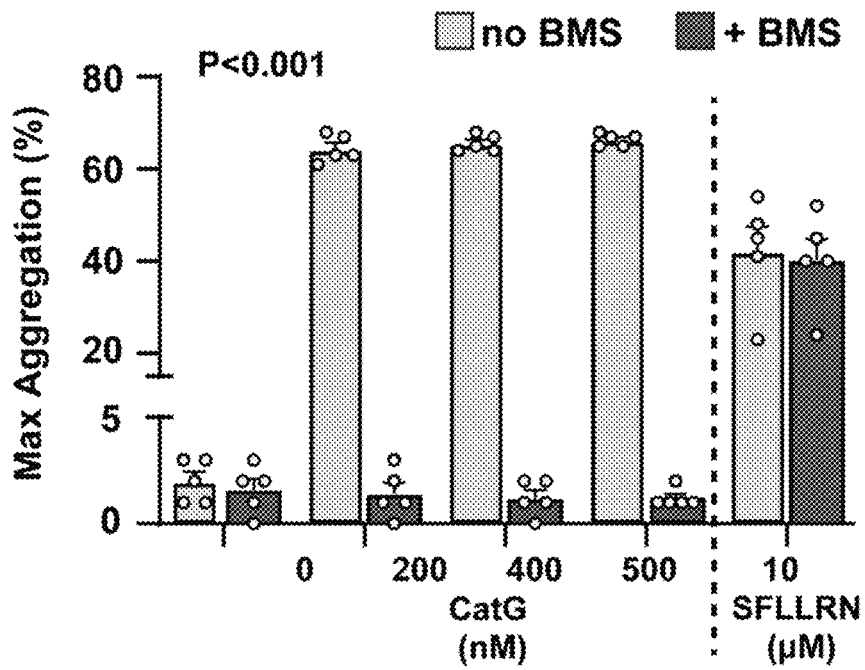
Figure 2B:
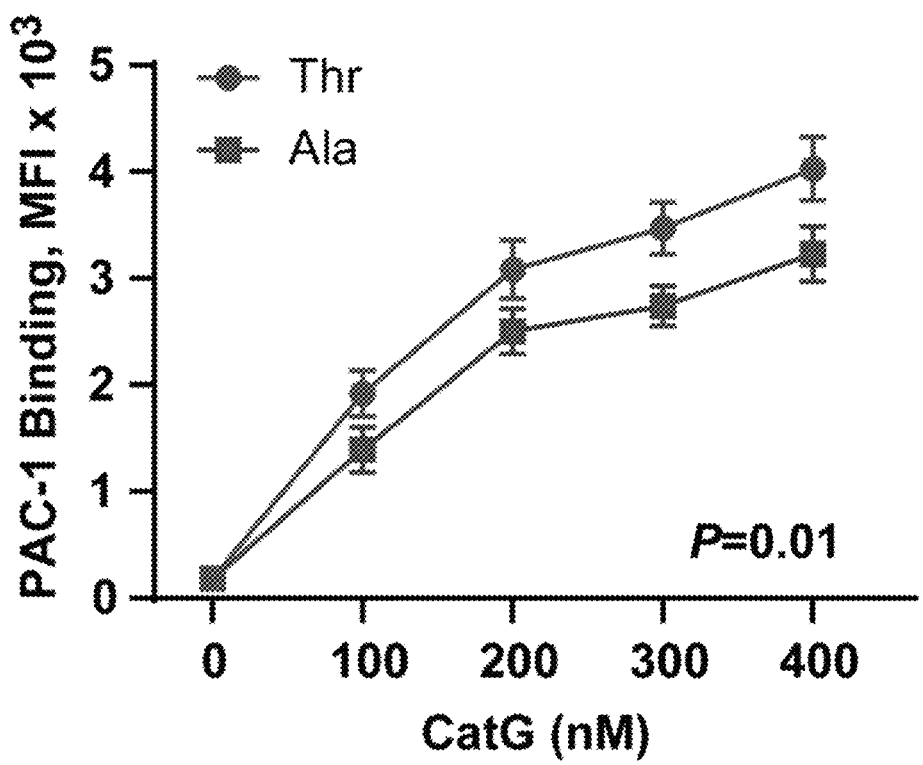
Figure 3:
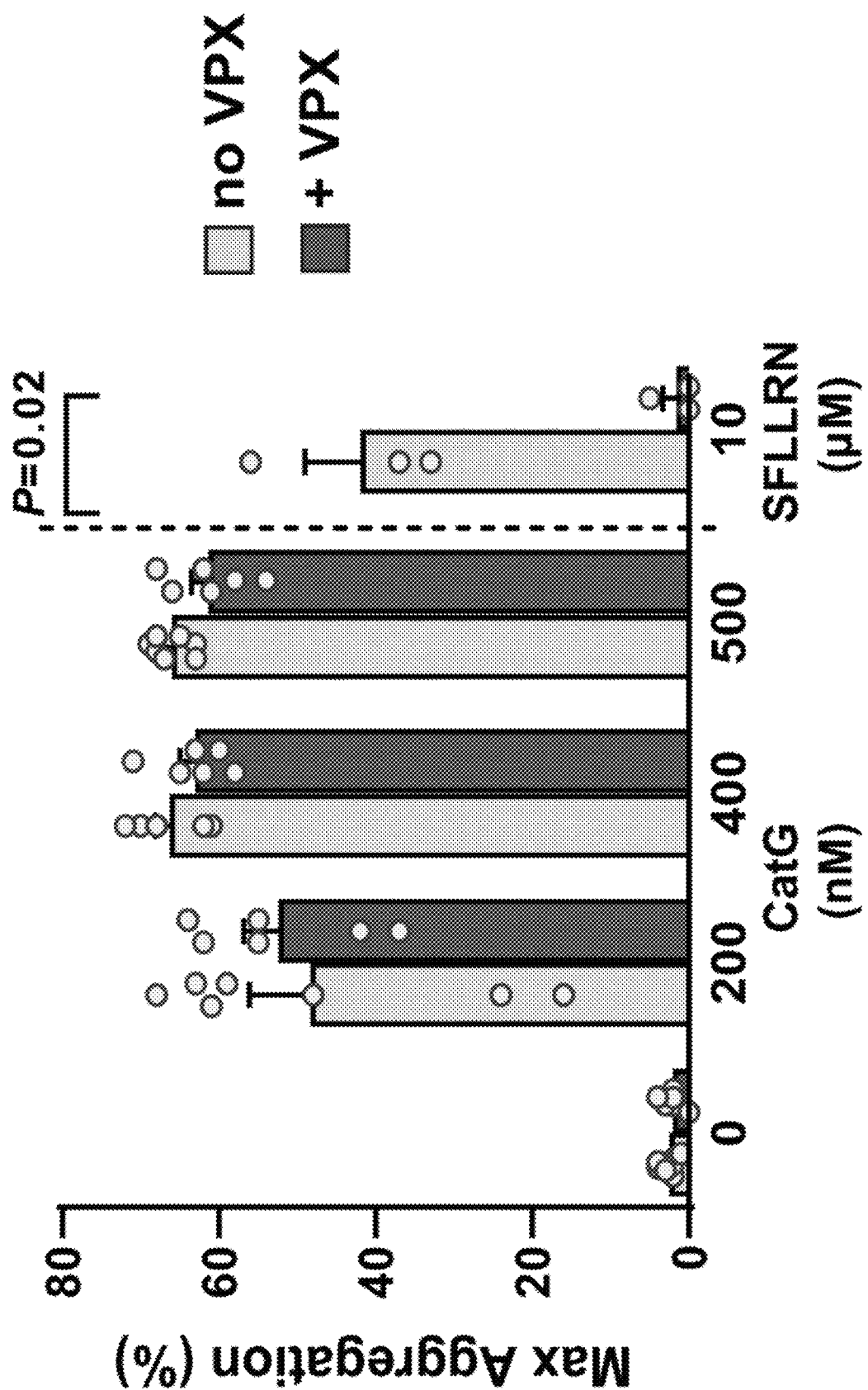
FIG. 3 is a bar chart showing that CatG platelet aggregation is not dependent on PAR1. Washed platelets were treated with varying concentrations of CatG in the presence or absence of the PAR1 inhibitor, vorapaxar (100 nM VPX; n=7 no VPX, n=6+VPX) and maximum (max) platelet aggregation (%+SEM) recorded. The PAR1 activation peptide (SFLLRN (SEQ ID NO: 28) 10 µM) served as a as a positive control to indicate that the concentration of VPX efficiently ablated PAR1 activation. n=3 different subjects.
Figure 4:
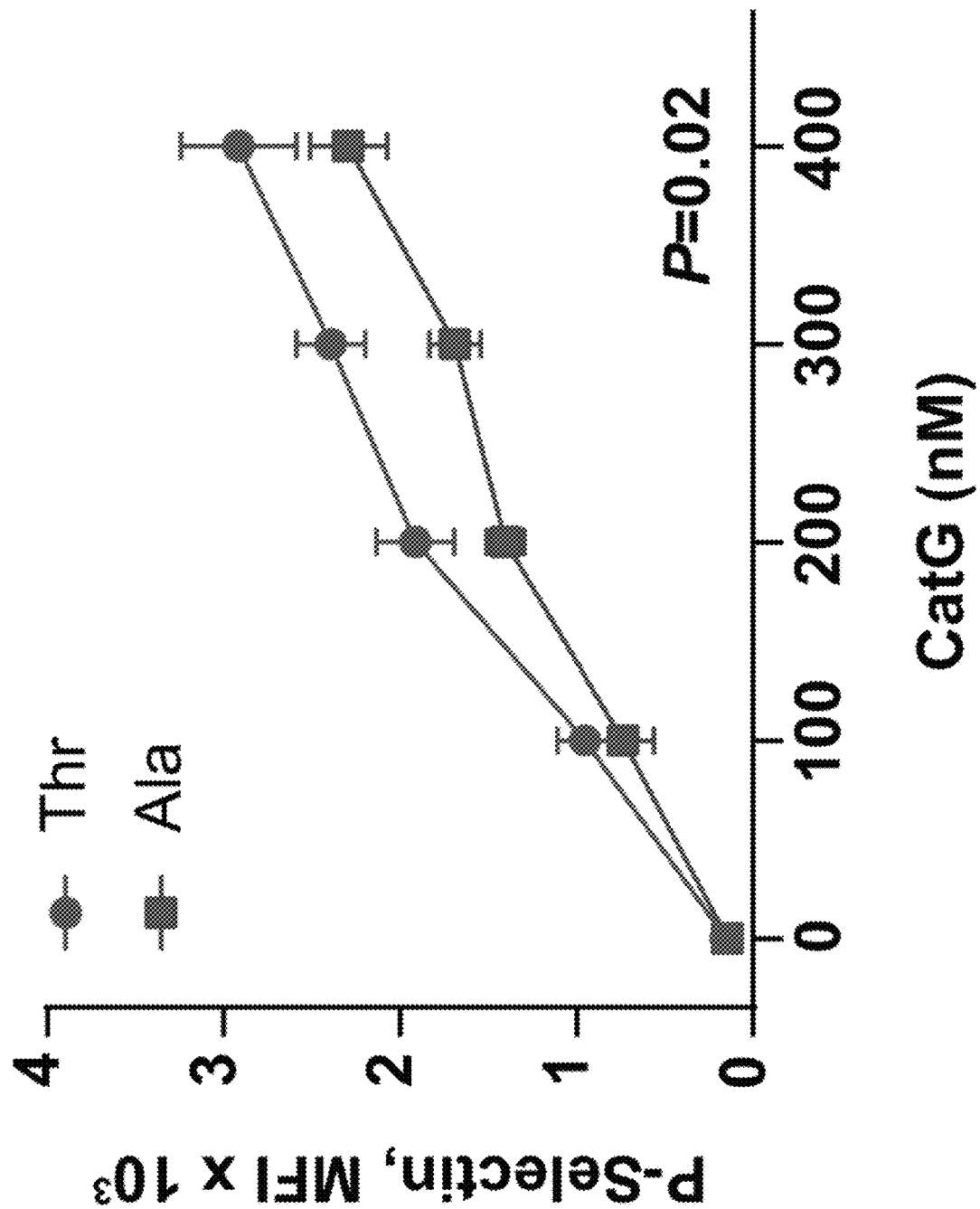
FIG. 4 is a graph showing the effect of PAR4 Ala120Thr variant on CatG-induced platelet P-selectin expression. Washed platelets were stimulated with increasing concentrations of CatG and platelet activation was measured by P-selectin (Ala: n=9 different homozygous $Ala^{120}$ subjects; Thr: n=9 different homozygous $Thr^{120}$ subjects) and displayed as MFI (mean+SEM).

Of the major serine proteases released from neutrophils, CatG was the only protease to induce platelet aggregation and αIIbβ3 activation (FIGS. 1A-1D). FIG. 1A shows the effect of neutrophil activation on platelet activation is mediated in large part by CatG. Using PAR-specific inhibitors, it was observed that CatG-dependent platelet activation was mediated by PAR4 and not PAR1 (FIG. 2A; FIG. 3). Because platelet-neutrophil interactions are critical in stroke pathophysiology and a common PAR4 Ala$^{120}$Thr variant has been associated with human stroke risk, the effect of this variant on CatG-induced platelet activation was studied. Compared with platelets from homozygous Ala$^{120}$ individuals, CatG stimulation of platelets homozygous for the racially divergent and hyperreactive PAR4 Thr$^{120}$ variant demonstrated modest but significantly greater αIIbβ3 activation and P-selectin expression (FIG. 2B; FIG. 4). Thus, neutrophil-released CatG may contribute to the increased stroke risk associated with the PAR4Thr$^{120}$ variant.

Figure 2C:
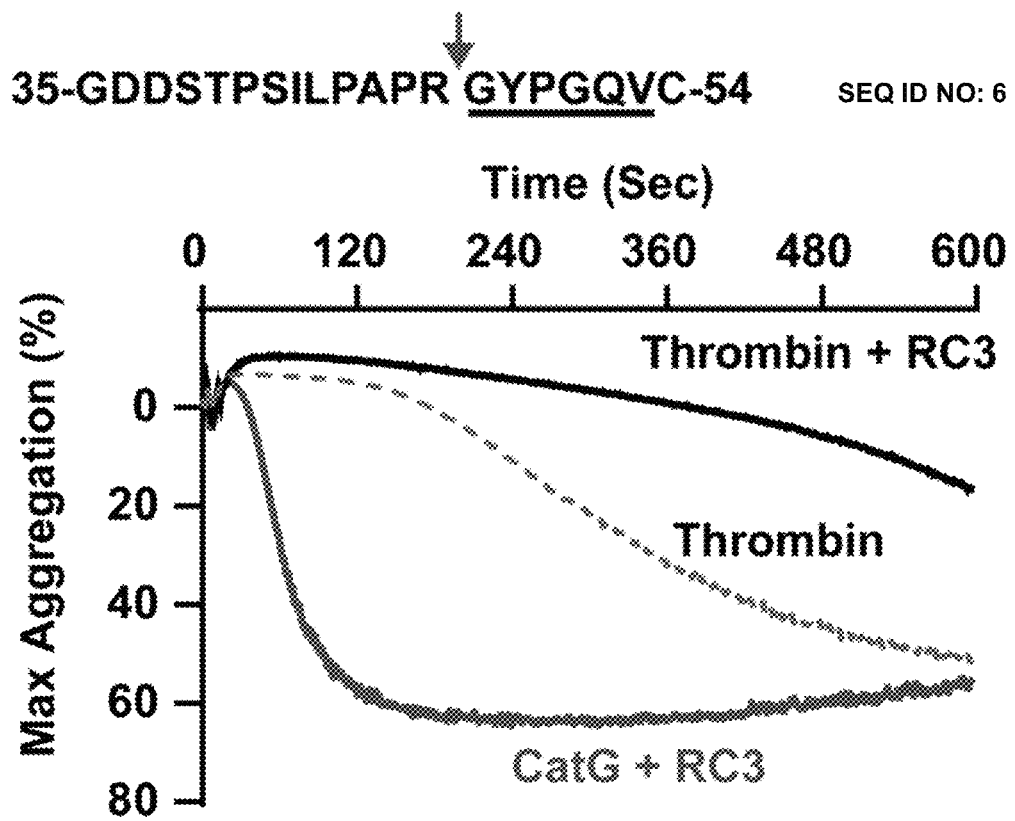
Figure 2D:
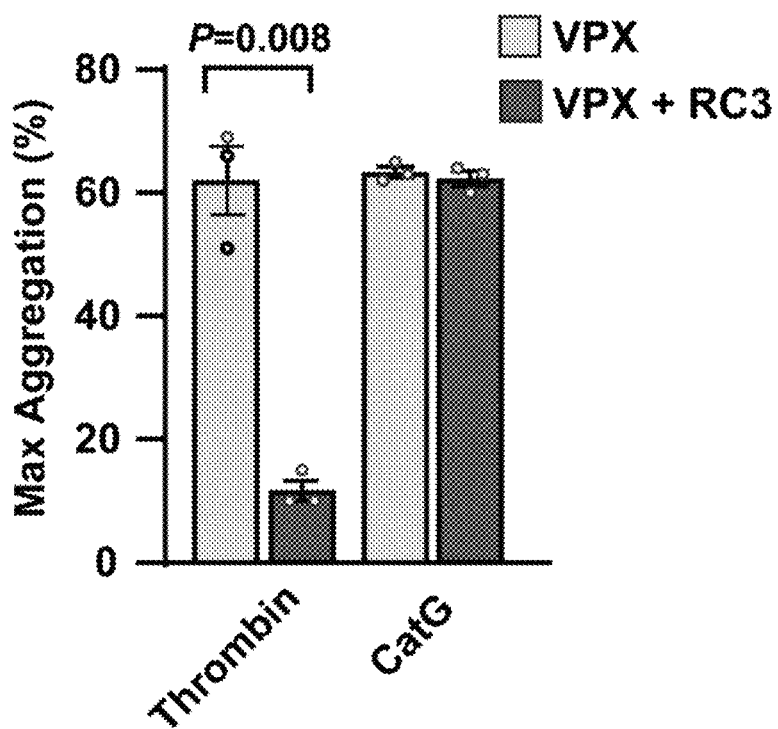
Figure 5:
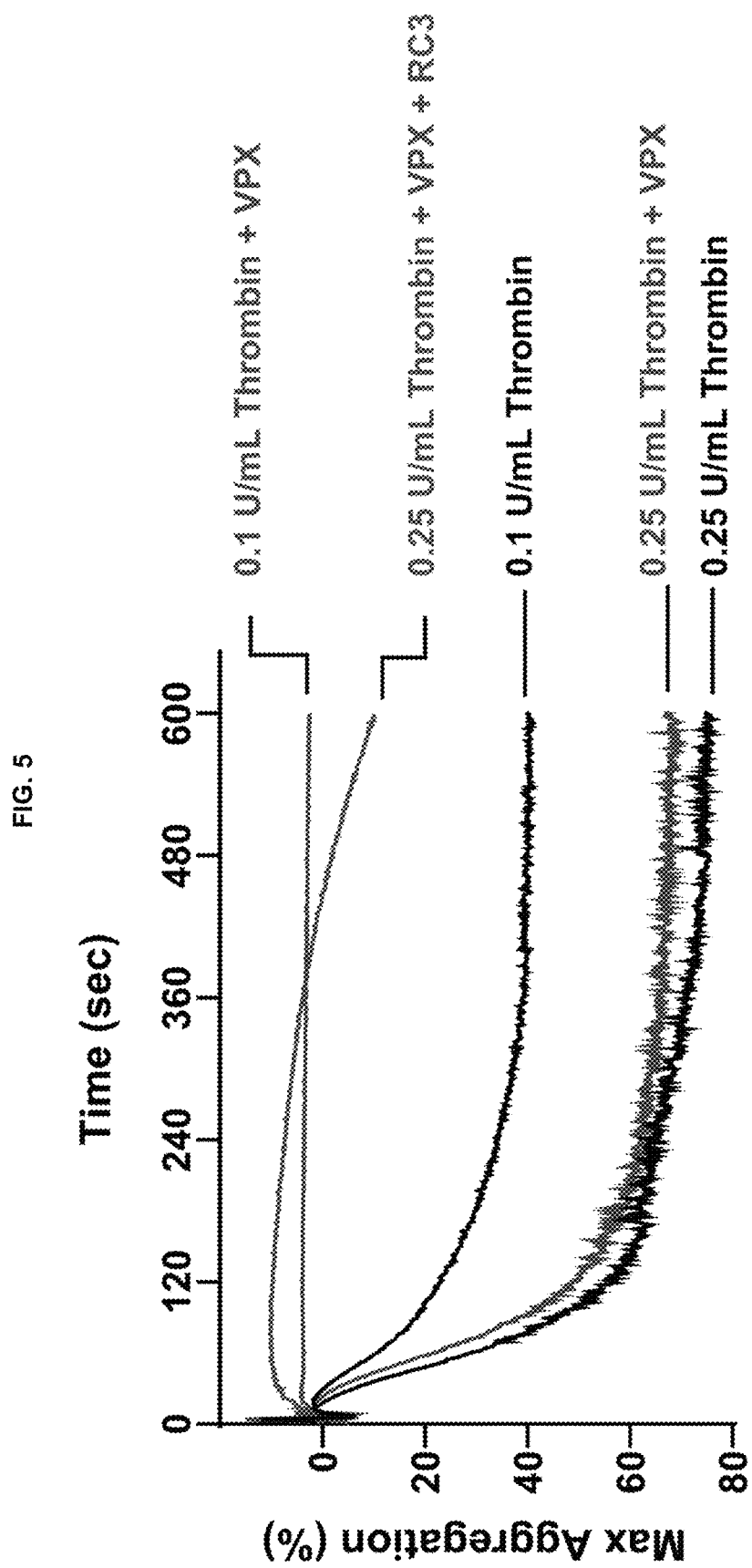
FIG. 5 is a graph showing PAR activation induced by different concentrations of thrombin. Representative tracing (of independent experiments) of washed platelets treated with the indicated concentrations of thrombin in the presence or absence of PAR1 inhibitor vorapaxar (100 nM VPX) or PAR4-blocking antibody (RC3). Note 100 nM VPX abolished 0.1 U/mL thrombin-induced platelet aggregation.

Thrombin cleavage of PAR4 at Arg$^{47}$-Gly$^{48}$ is blocked by the monoclonal antibody RC3.6 RC3 had little effect on CatG-induced platelet aggregation despite largely abolishing thrombin-induced aggregation (FIGS. 2C-2D; FIG. 5) (note thrombin activation of PAR1 was blocked in FIGS. 2C-2D, as determined by FIG. 5). These results suggest CatG cleaves PAR4 at a site different than thrombin. It is not clear why this data apparently differ from previous observations using a polyclonal antibody to PAR4 (French et al., Blood Adv. 2018; 2(11): 1283-1293; Sambrano et al., J Biol Chem. 2000; 275(10):6819-6823) since the antibodies were raised against the same sequence, but perhaps the polyclonal antibody also blocked the CatG cleavage site while monoclonal RC3 does not.

Example 3

CatG Proteolysis of PAR4 N-Terminal Extracellular Sequence

Figure 2G:
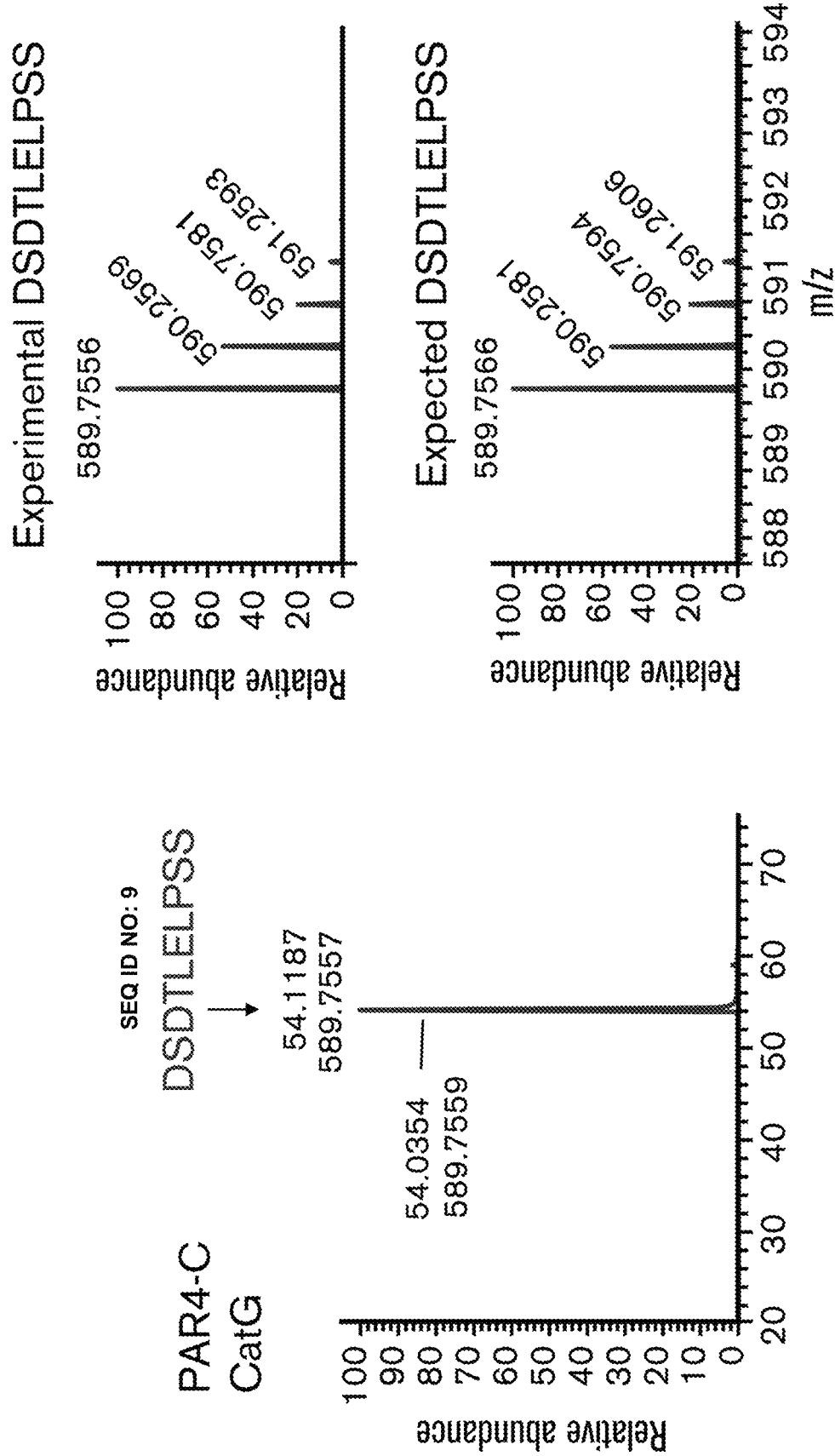
Figures 6A, 6B:
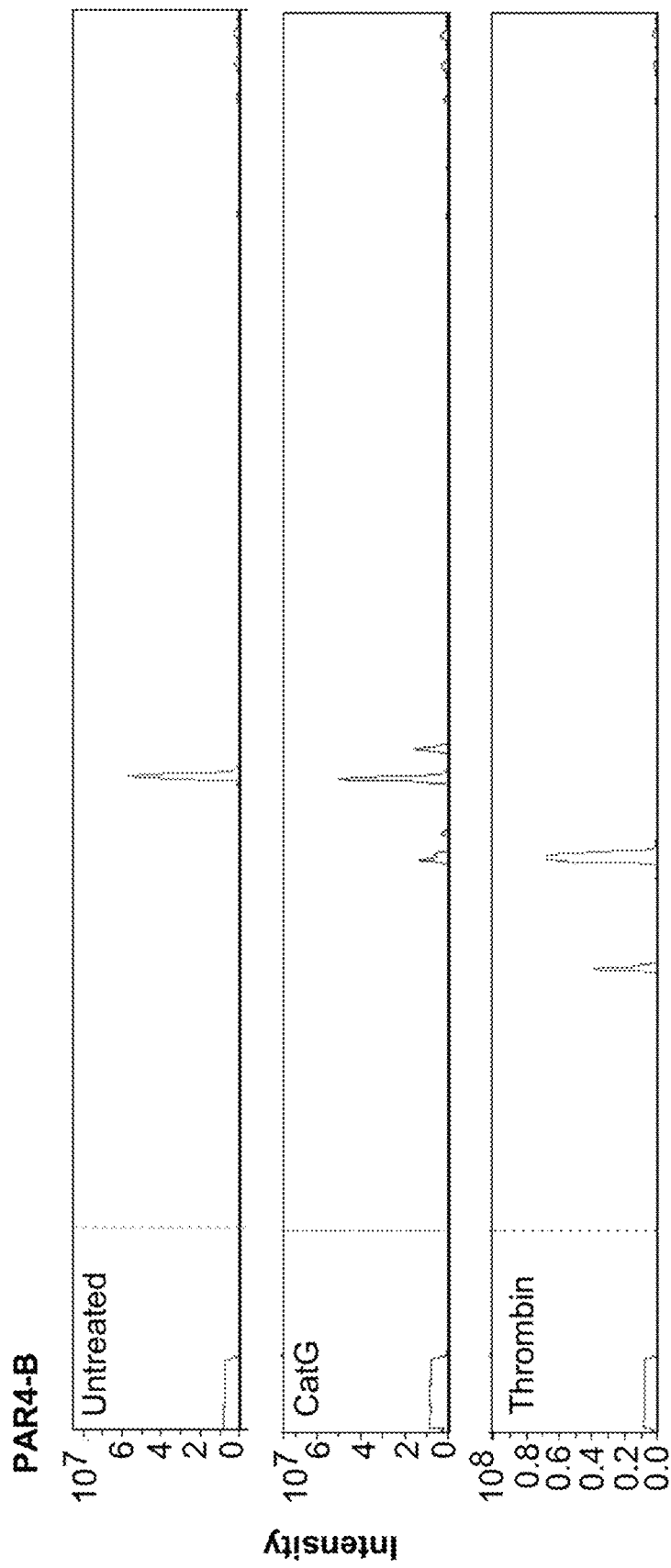
FIGS. 6A-6B show that cathepsin G has minimal proteolytic effects on a PAR4-B peptide containing the canonical thrombin cleavage site.

To examine the possible cleavage fragments generated by CatG, two portions of the PAR4 extracellular N-terminus were synthesized and analyzed by LC-MS/MS: PAR4-B (SEQ ID NO: 7) containing the thrombin cleavage site, and PAR4-C(SEQ ID NO: 8), downstream of the thrombin cleavage site (FIG. 2E). As expected, PAR4-B was cleaved by thrombin between amino acids Arg47 and Gly48, while little cleavage was observed with CatG (FIG. 6). In contrast, thrombin failed to cleave PAR4-C, while CatG cleavage generated several fragments, including DSDTLELPSS (FIG. 2G; SEQ ID NO: 9). Identification of the DSDTLELPSS (SEQ ID NO: 9) fragment (amino-terminal sequence of PAR4-C) indicated CatG cleavage between Ser67 (S67)-Arg68 (R68). As a control, in the absence of thrombin or CatG, PAR4-B and PAR4-C remained intact in these analyses (FIG. 2F; FIG. 6).

Example 4

Figure 2H:
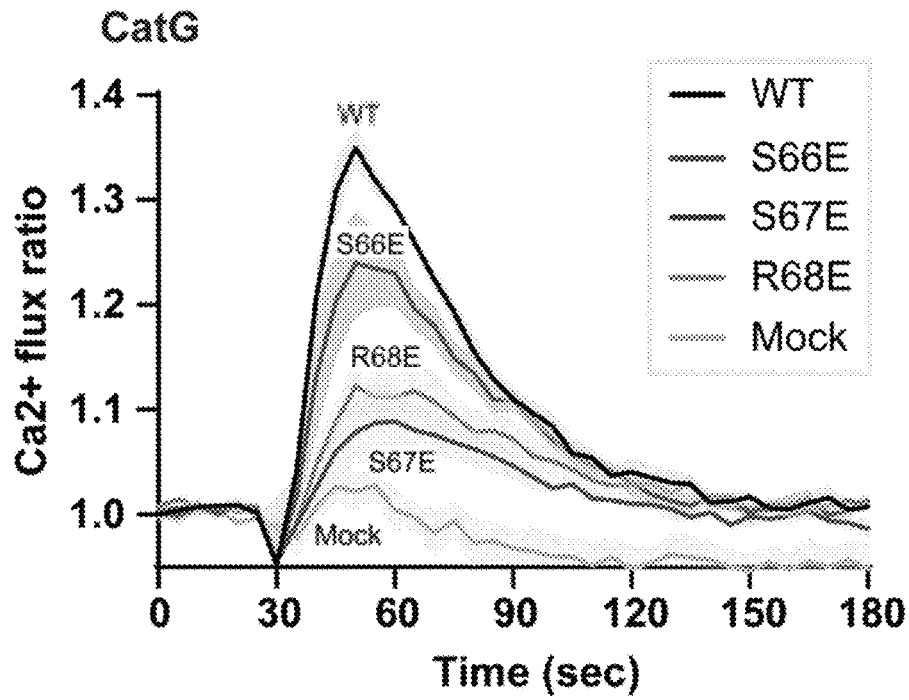
Figure 2I:
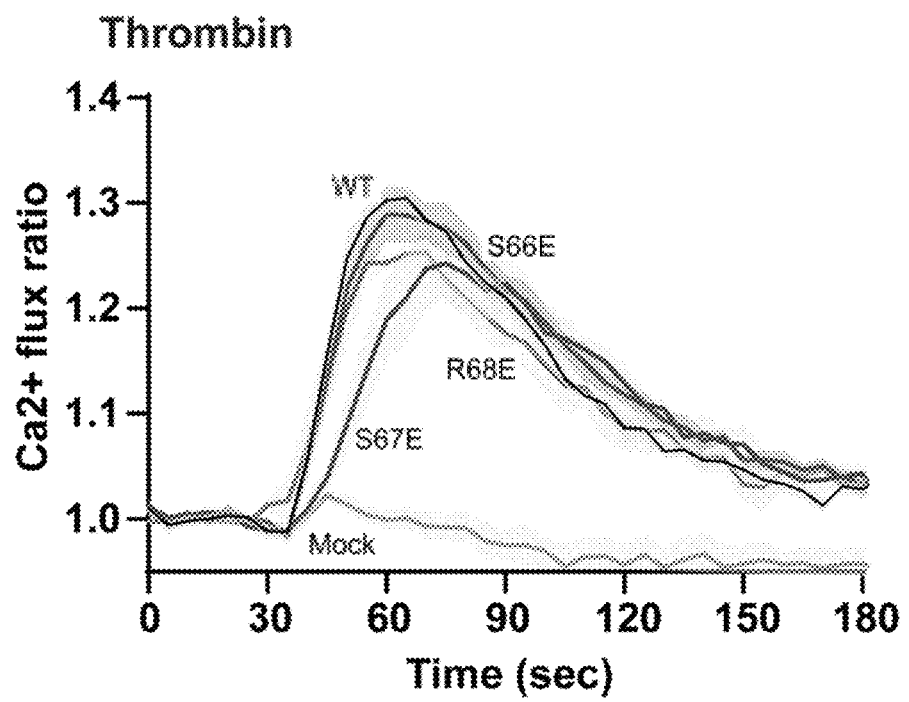

Mutations of Amino Acids Ser$^{67}$ and Arg$^{68}$ Decrease CatG-Stimulated PAR4-Mediated Calcium Signaling To specifically examine if CatG induces PAR4 activation and signaling by cleaving Ser$^{67}$-Arg$^{68}$, calcium flux was assessed using various PAR4 mutants. HEK cells transfected with WT PAR4 demonstrated increased calcium flux when treated with CatG compared with mock transfection (FIG. 2H). CatG activation of HEK cells expressing either PAR4 mutated Ser$^{67}$ to Glu (S67E) or Arg$^{68}$ to Glu (R68E) resulted in significantly less calcium flux than WT ($P<0.001$) (FIG. 2H). Notably, the PAR4 S67E and R68E mutants induced minimal calcium flux above baseline, such that we cannot exclude other minor CatG cleavage sites indicated by the mass spectrometry data (FIG. 2H; FIG. 6) could induce receptor activation, as has been shown with elastase-cleavage of PAR2. Since neighboring amino acids can be critical in protease cleavage, a Ser$^{66}$ (S66E) mutant was generated that showed a slight decrease in CatG-induced calcium flux compared with WT and a significantly greater calcium flux than mock transfection (FIG. 2H). None of the PAR4 mutants were significantly different than WT when stimulated by thrombin in the presence of a PAR1 inhibitor (FIG. 2I). Taken together, these data support CatG, but not thrombin, cleavage of PAR4 between Ser$^{67}$-Arg$^{68}$.

Example 5

Functional Characterization of CatG-Generated PAR4 Tethered Ligand

Figure 7A:
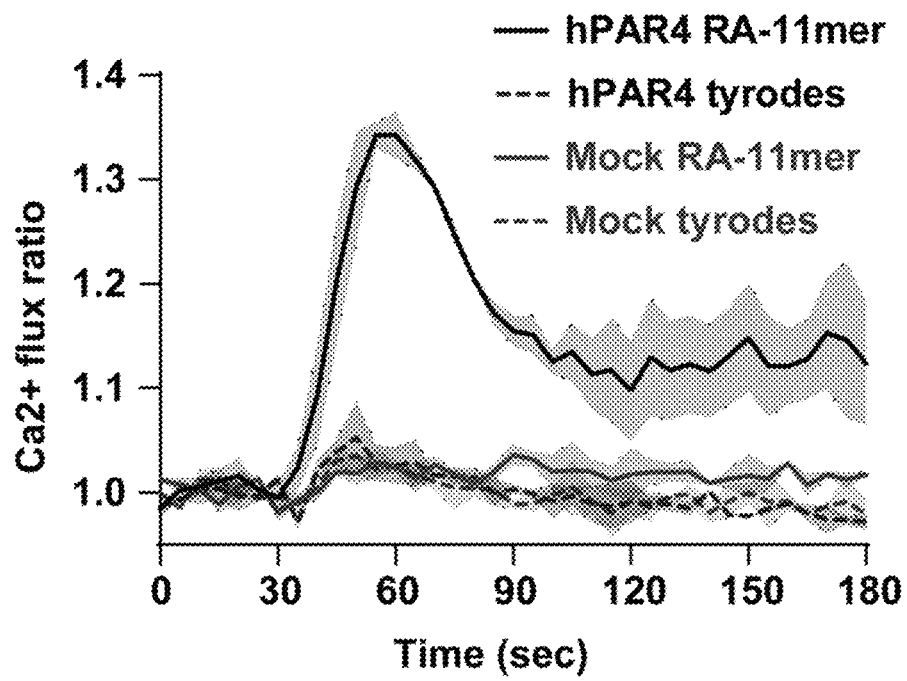
FIGS. 7A-7L show that CatG-generated PAR4 tethered ligand RALLLGWVPTR (SEQ ID NO: 1) induces platelet activation and aggregation.
Figure 7B:
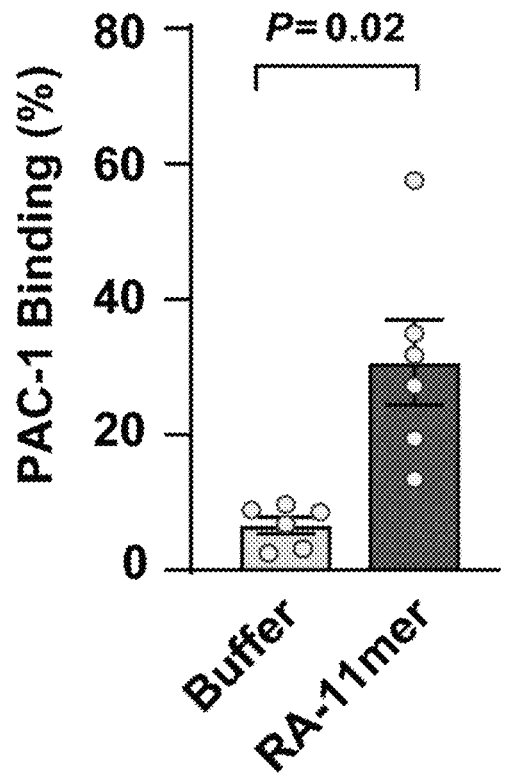
Figure 7C:
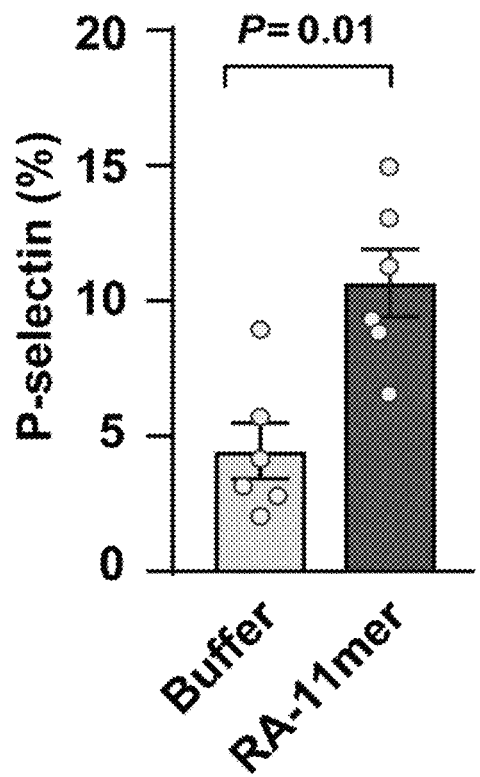
Figure 7D:
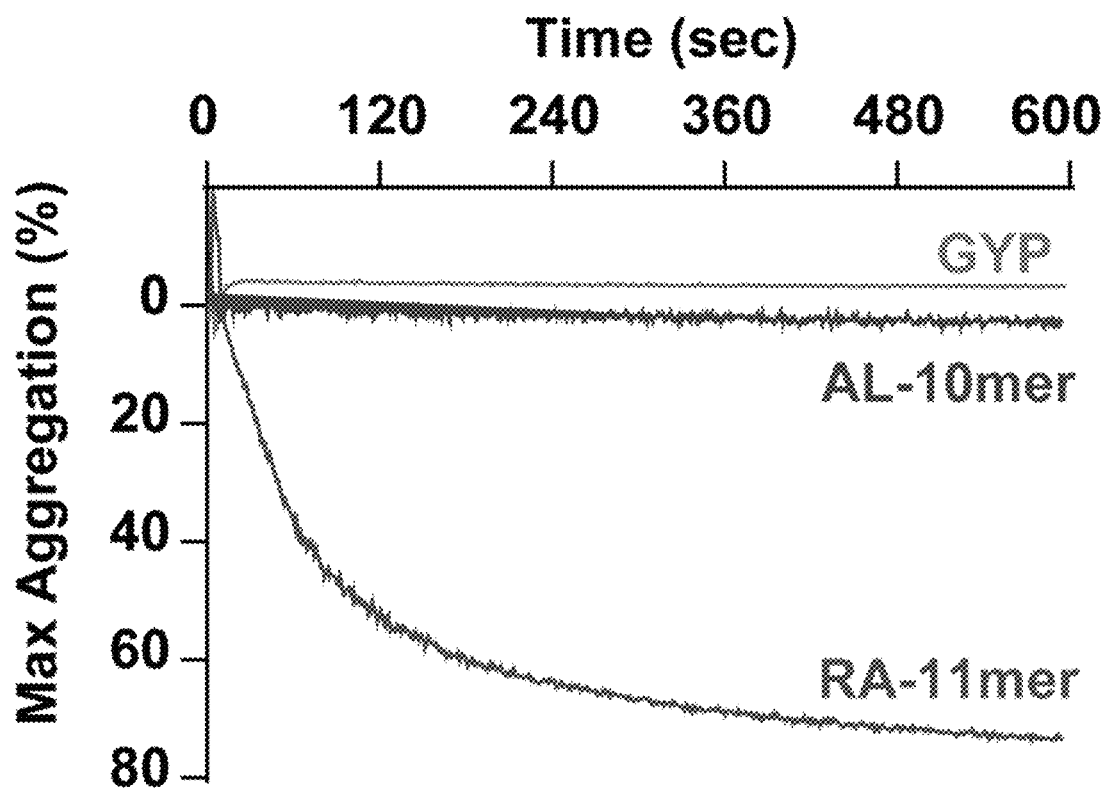
Figure 7E:
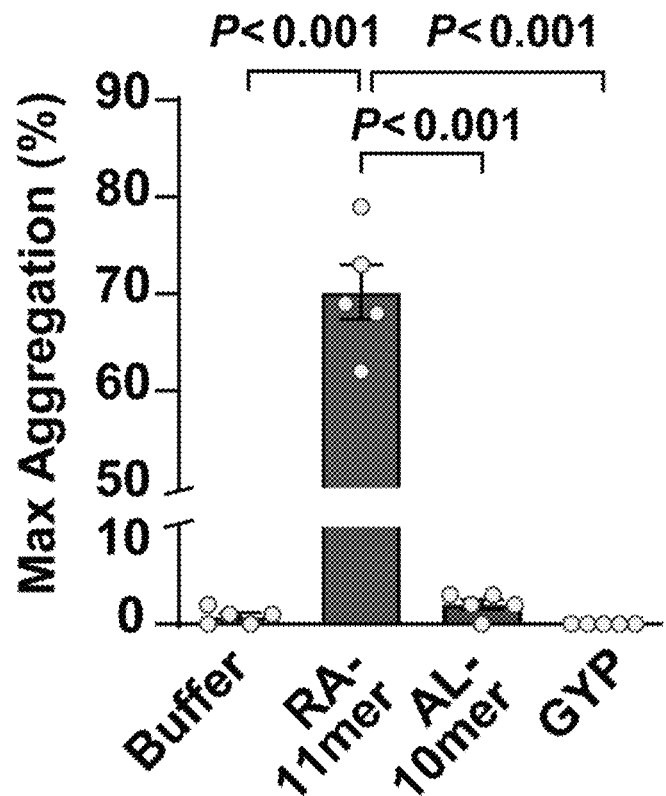
Figure 7F:
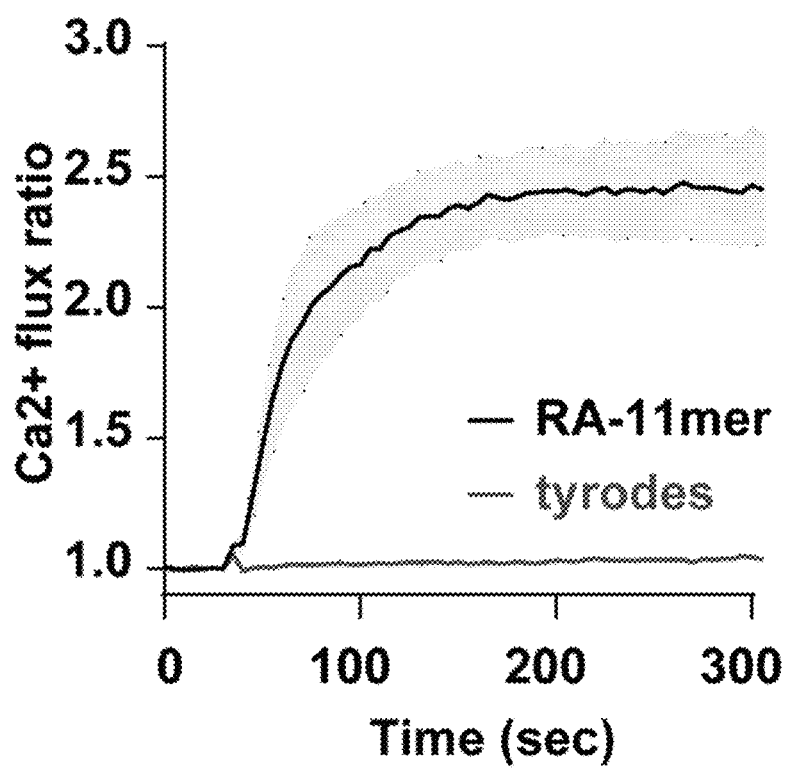
Figure 8:
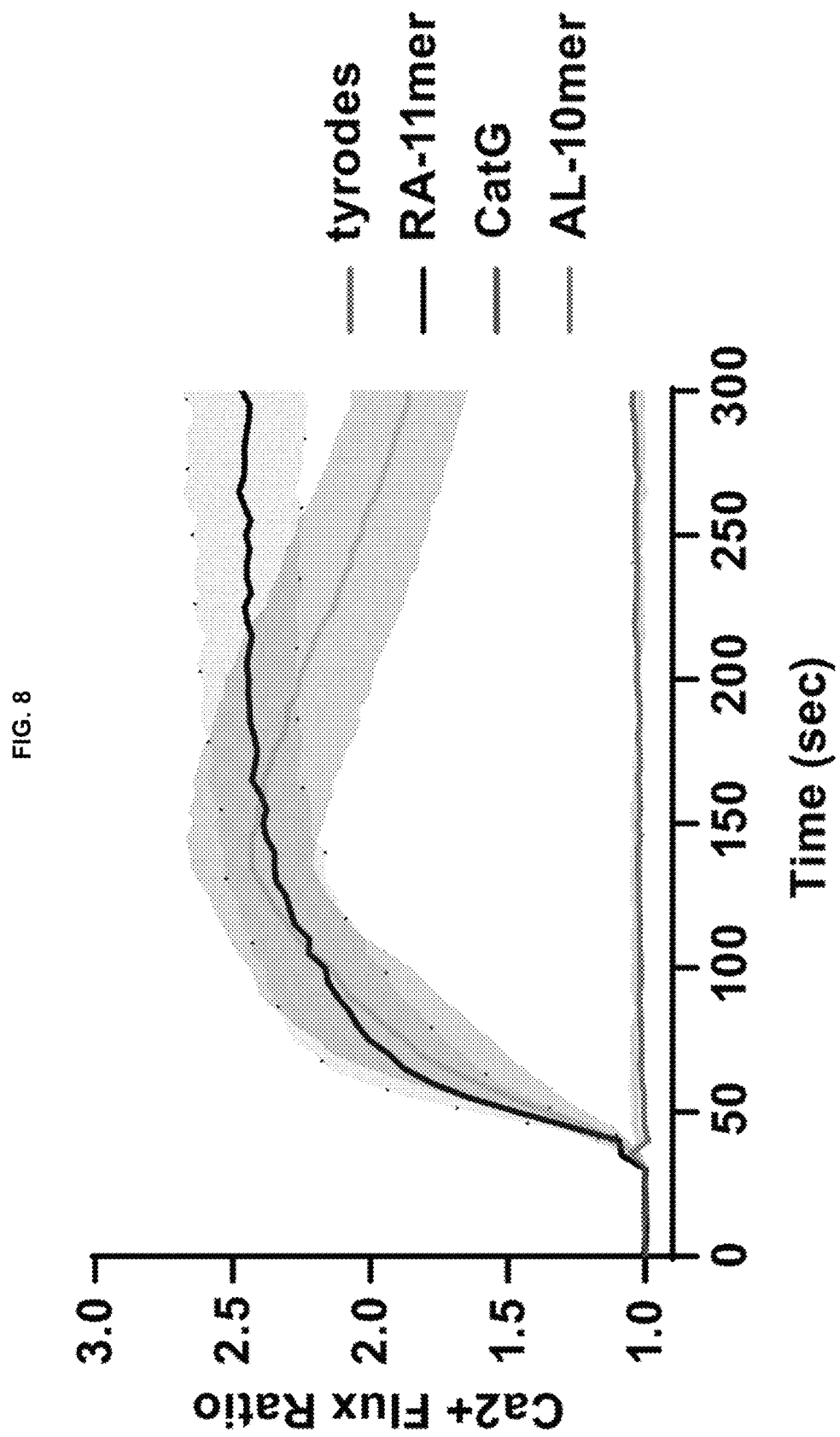
FIG. 8 is a graph showing that platelet calcium is induced by RA-11mer having the amino acid sequence of SEQ ID NO: 1 and CatG. Washed platelets were loaded with FURA2-AM for 1 hour. Platelets were washed, resuspended in Tyrodes buffer at 4x10⁸ platelets/mL, treated with RALLLGWVPTR (SEQ ID NO: 1) (RA-11mer, 2 mM), CatG (500 nM), ALLLGWVPTR (SEQ ID NO: 2) (AL- 10mer, 2 mM), or Tyrodes buffer, and calcium flux was measured. The mean+SEM is shown. n=3-4 per group.

A synthetic peptide RALLLGWVPTR (SEQ ID NO: 1) representing the CatG-generated PAR4 tethered ligand was synthesized to assess its potential functionality. RALLLGWVPTR (SEQ ID NO: 1) induced calcium flux in HEK cells transfected with WT PAR4 compared with mock, indicating the tethered ligand induces signaling through PAR4 (FIG. 7A). Platelets treated with RALLLGWVPTR (SEQ ID NO: 1) demonstrated increased integrin activation, α granule release, and platelet aggregation (FIGS. 7B-7E). In addition, RALLLGWVPTR (SEQ ID NO: 1) induced a significant and sustained calcium flux in platelets similar to other peptide-tethered ligands (FIG. 7F). Peak calcium flux was similar between CatG and RALLLGWVPTR (SEQ ID NO: 1), and consistent with previous literature, CatG-induced platelet calcium flux decreased over time (FIG. 8).

Figure 9:
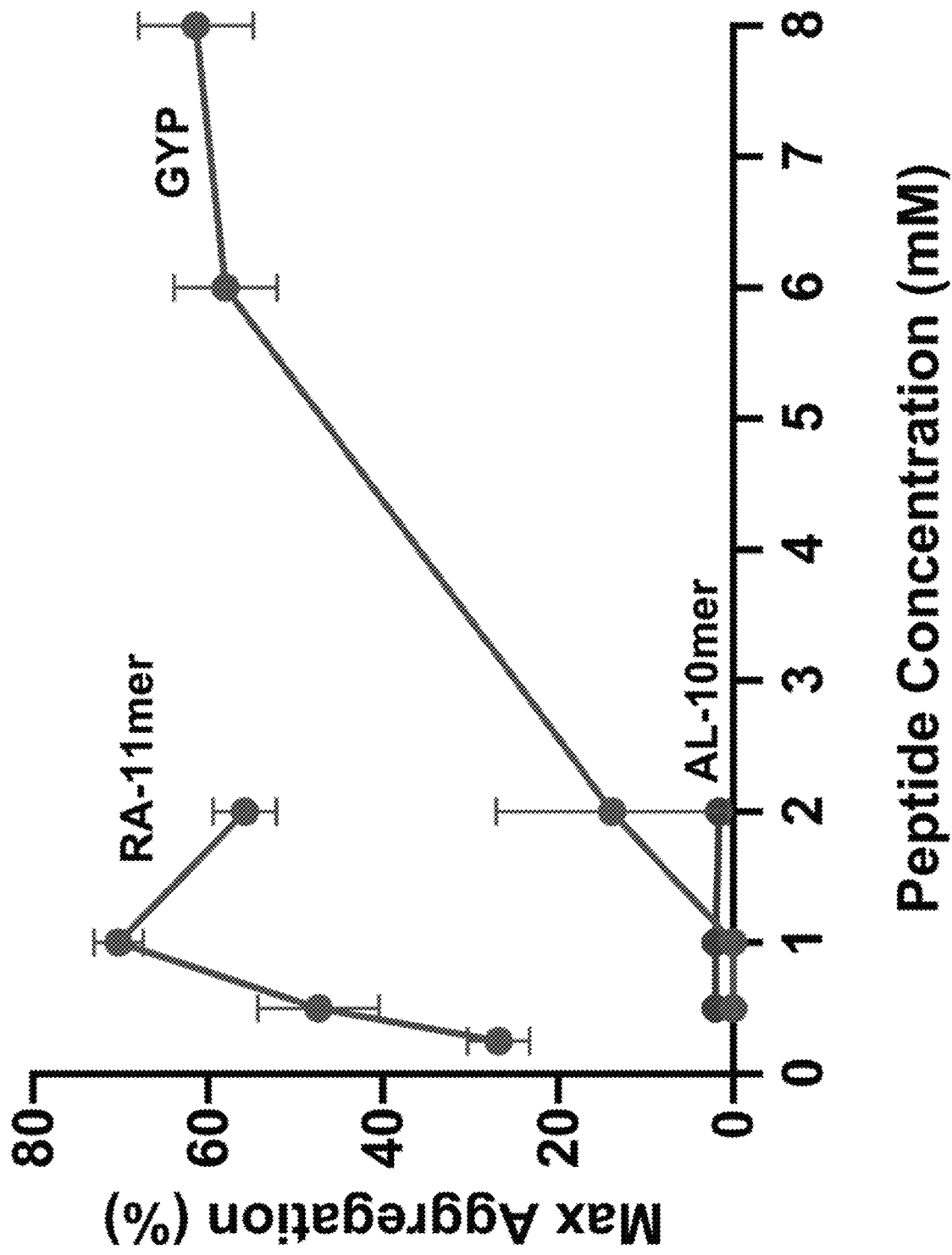
FIG. 9 is a graph showing that platelet aggregation is induced by different concentrations of PAR4 peptides. Washed platelets were treated with the indicated concentrations of GYPGQV (SEQ ID NO: 5) (GYP), RALLLGWVPTR (SEQ ID NO: 1) (RA-11mer), or ALLLGWVPTR (SEQ ID NO: 2) (AL-10mer) and maximum (max) aggregation measured (%+SEM). n=5 per group.

LC-MS/MS analysis also indicated a minor CatG cleavage between $Arg^{68}$ and $Ala^{69}$ under the conditions of the experiment, so an ALLLGWVPTR (SEQ ID NO: 2) 10mer was also synthesized. However, platelets exposed to ALLLGWVPTR (SEQ ID NO: 2) displayed no discernable platelet aggregation or calcium flux (FIGS. 7D-7E; FIG. 8) independent of peptide concentration (FIG. 8 and FIG. 9). Notably, 1 mM RALLLGWVPTR (SEQ ID NO: 1) produced maximal platelet aggregation, while 6 mM GYPGQV (SEQ ID NO: 5) (the thrombin-generated PAR4 tethered ligand) was necessary to induce maximal platelet aggregation consistent with previous literature, demonstrating high concentrations of GYPGQV (SEQ ID NO: 5) are needed to induce receptor activation (FIGS. 7D-7E; FIG. 9). The CatG-generated tethered ligand appears to be a more potent activator of PAR4 than the thrombin-generated tethered ligand, but the CatG enzyme is much less potent than the thrombin enzyme. Perhaps thrombin has greater affinity for the PAR4 extracellular domain than does CatG.

Figure 7G:
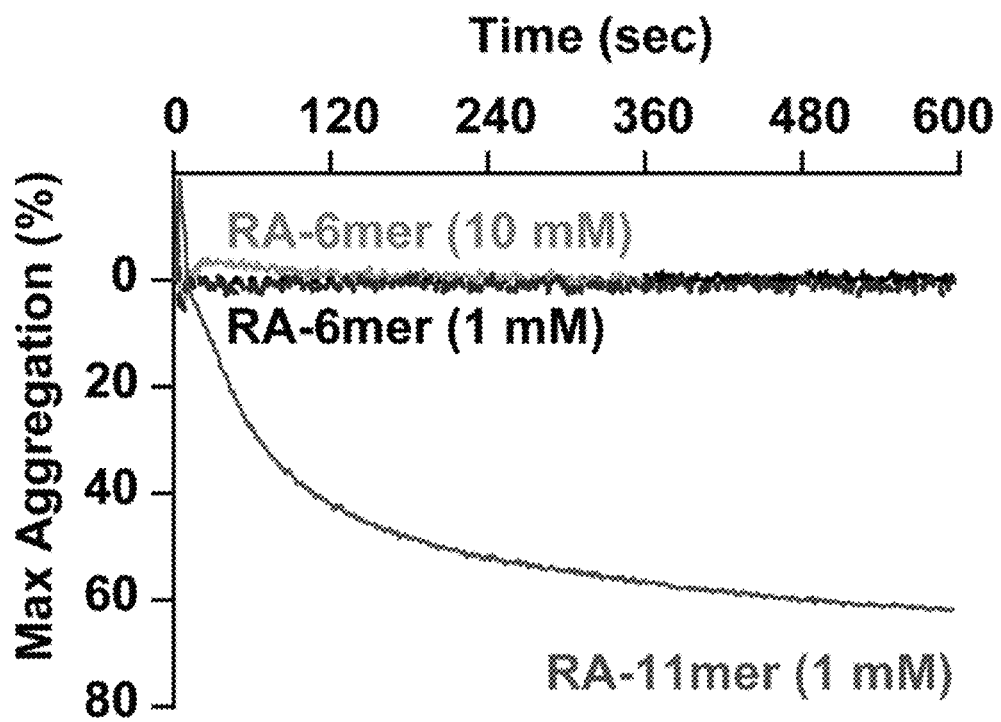
Figure 7H:
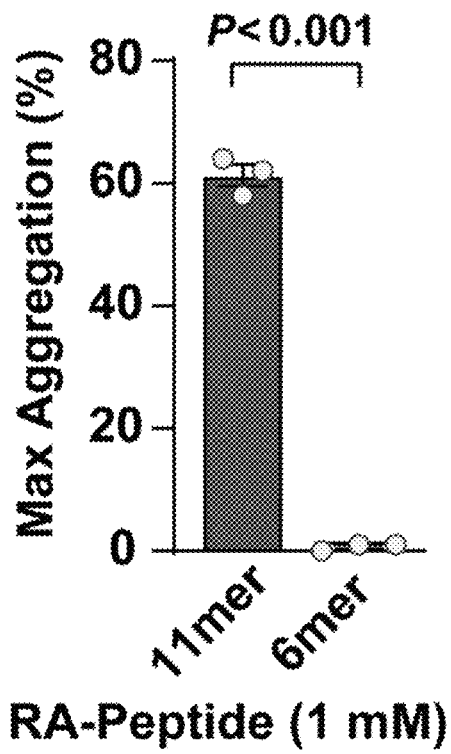

PAR4 signaling can be induced by the thrombin-tethered ligand with as few as 6 amino acids (GYPGQV (SEQ ID NO: 5)), but a 6mer from the CatG tethered ligand (RALLLG (SEQ ID NO: 4)) was not able to induce platelet aggregation (FIGS. 7G-7H). We also synthesized an intermediate length peptide, RALLLGWV 8mer (SEQ ID NO: 3), but were unable to test its activating potential due to its inability to go into solution despite numerous attempts with different solvents. Having said that, perhaps the hydrophobic portion of the C-terminus of RALLLGWVPTR (SEQ ID NO: 1) stabilizes the tethered ligand on the platelet plasma membrane.

Example 6

Genetics of PAR4 Variants

Figures 7I, 7J:
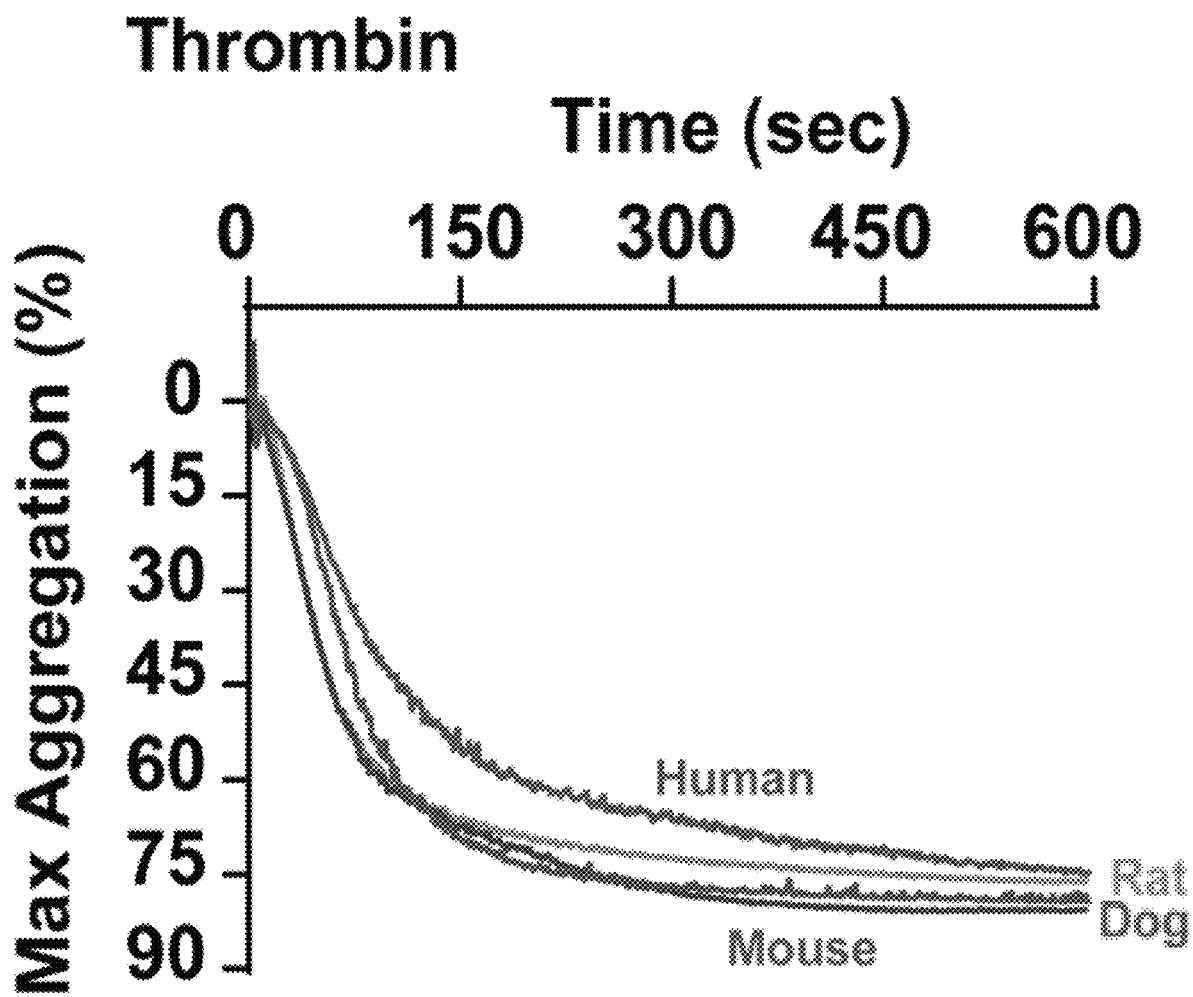
Figure 7K:
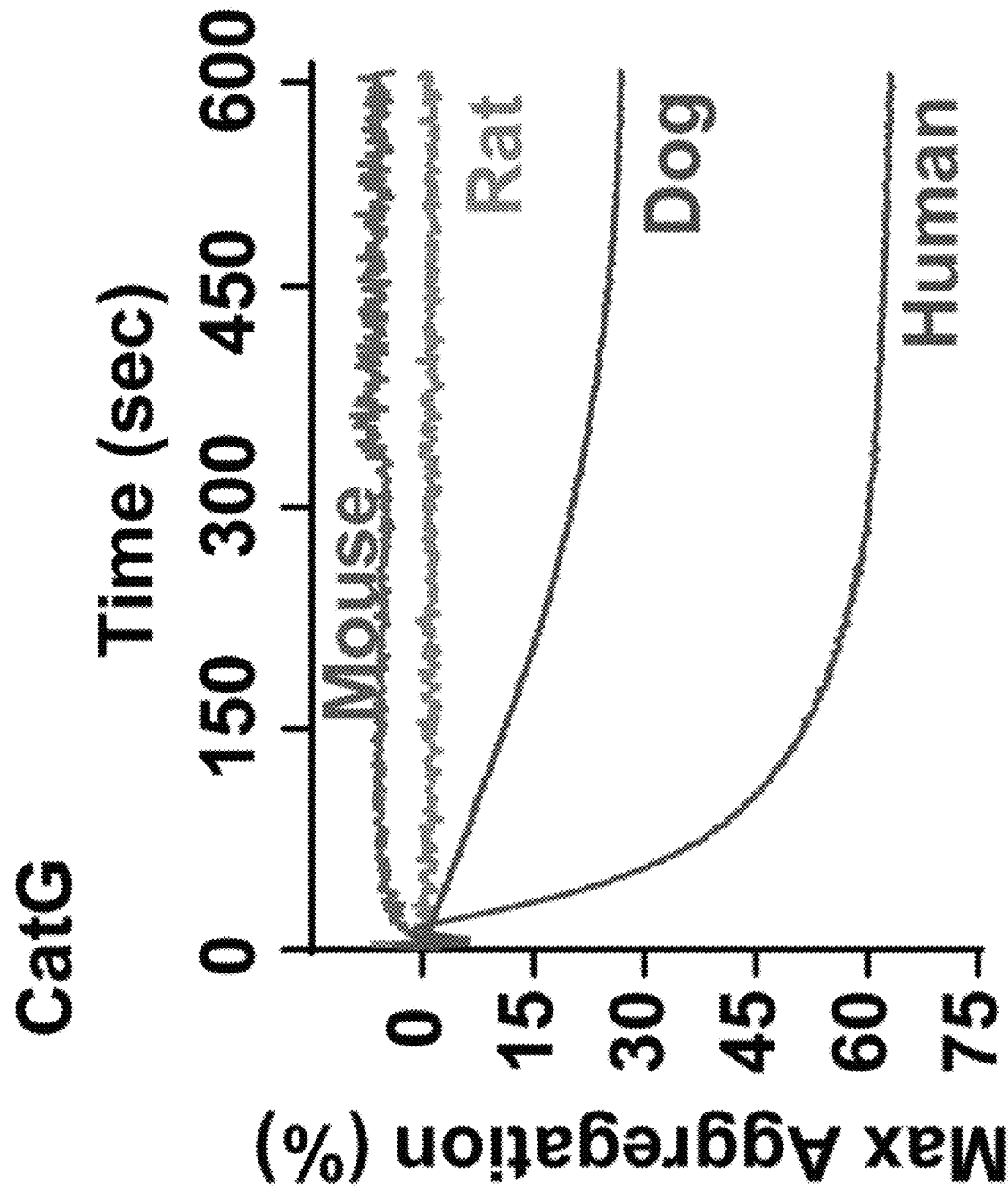
Figure 7L:
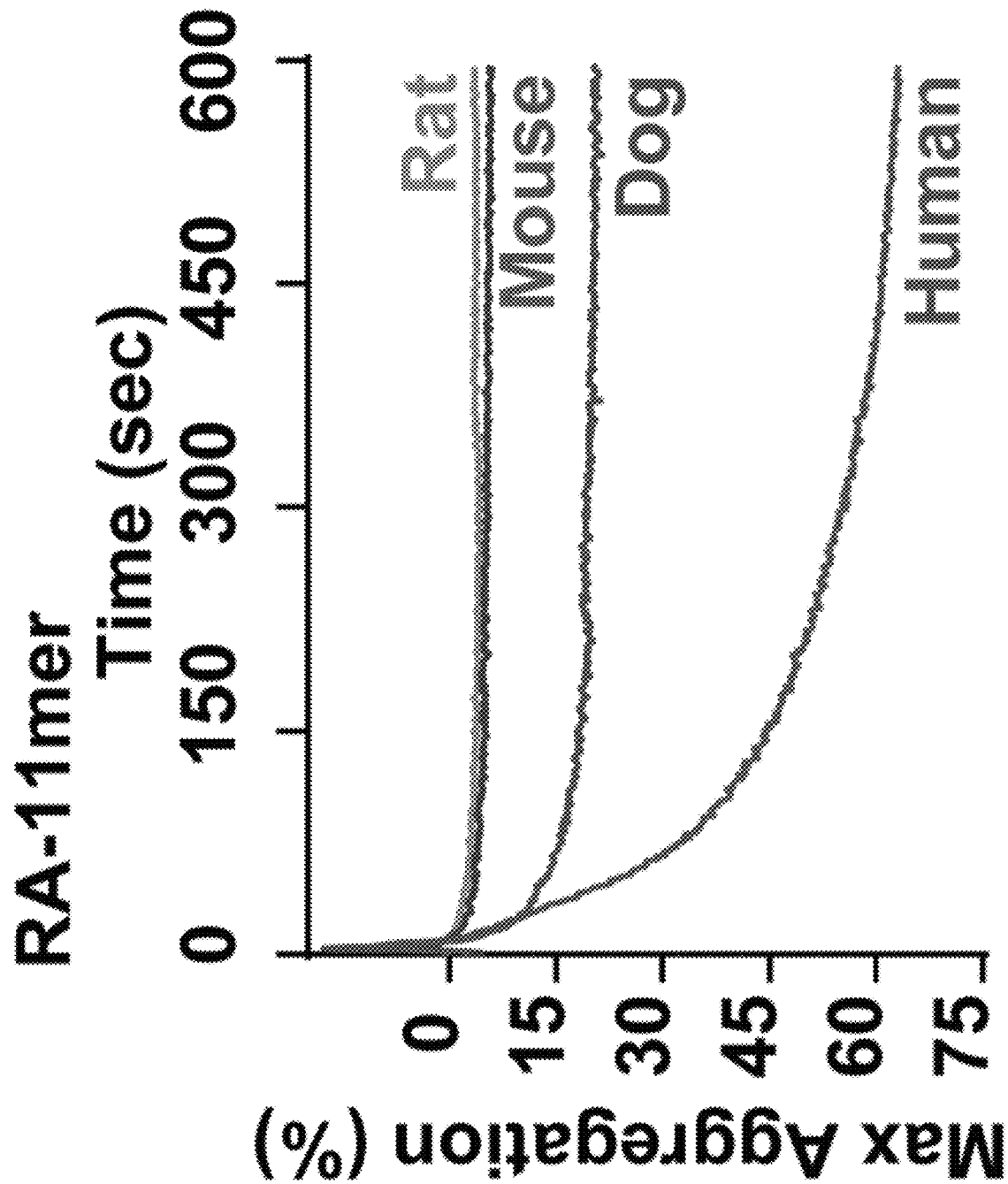

Conservation of amino acid sequence across species can be supportive and informative of sequence function. Table 1 shows the sequence alignments of PAR4 N-terminal from 12 animals (extracellular membrane is underlined), 4 of which are shown in FIG. 7I. Human thrombin induced platelet aggregation in humans, dogs, mice, and rats (FIG. 7J), whereas human CatG only induced platelet aggregation in humans and dogs (FIG. 7K). Similar to CatG, the RA-11mer having the amino acid sequence of SEQ ID NO: 1 induced aggregation only in humans and dogs (FIG. 7L). Dog platelets were not as responsive to human CatG, perhaps due to inefficient binding of human CatG to dog PAR4 or the substitution of an alanine for a proline in the dog PAR4 sequence. Furthermore, the human RA-11mer having the amino acid sequence of SEQ ID NO: 1 could be less effective binding to the dog PAR4 extracellular domain that mediates the signaling response to the dog tethered ligand. This genetic data lends support to the mutagenesis and functional peptide data regarding the importance of $Arg^{68}$ in mediating CatG-mediated PAR4 cleavage and activation. Perhaps the positive charge of $Arg^{88}$ is important for the activity of the tethered ligand (mouse Gln is uncharged while rat Glu is negatively charged).

TABLE 1

Sequence alignments of PAR4 across species

| | | thromb cleav RG<br>Hsap SR is novel CatG cleavage site (S67/R68) | SEQ ID NO: |
|---|---|---|---|
| human | Hsap | 37-<br>DSTPSILPAPRGYPGQVCANDSDTLELPDSSRALLLGWVPT<br>RLVPALYGLVLVVGLPANGLALWVLATQ | 15 |
| gorilla | Ggor | DSTPSILPAPRSYPGQVCANDSDTLELPDSSRALLLGWVPT<br>RLVPALYGLVLVVGLPANGLALWVLATQ | 16 |
| human | Hsap | 37-<br>DSTPSILPAPRGYPGQVCANDSDTLELPDSSRALLLGWVPT<br>RLVPALYGLVLVVGLPANGLALWVLATQ | 15 |
| Olive baboon | Panu | DSTPSILPAPRGYPGQVCANDSDILELPDSSRALLLGWVPT<br>RLVPALYGLVLAVGLPANGLALWVLATR | 17 |
| human | Hsap | 37-<br>DSTPSILPAPRGYPGQVCANDSDTLELPDSSRALLLGWVPT<br>RLVPALYGLVLVVGLPANGLALWVLATQ | 15 |
| green monkey | Csab | ESTPSILPAPRGYPGQVCANDSDILELPDSSRALLLGWVPT<br>RLVPALYGLVLAVGLPANSLALWVLATR | 18 |
| human | Hsap | 37-<br>DSTPSILPAPRGYPGQVCANDSDTLELPDSSRALLLGWVPT<br>RLVPALYGLVLVVGLPANGLALWVLATQ | 15 |
| North greater galago | Ogar | EATLLFPQQPRSFPGCVFTNNSDILEIPDSSRALLLGWVPT<br>RLVPTLYGLVLVVGLPANGLALWVLATQ | 19 |

TABLE 1-continued

Sequence alignments of PAR4 across species

| | | thromb cleav RG Hsap SR is novel CatG cleavage site (S67/R68) | SEQ ID NO: |
|---|---|---|---|
| human | Hsap | 37-DSTPSILPAPRGYPGQVCANDSDTLELPDSSRALLLGWVPT RLVPALYGLVLVVGLPANGLALWVLATQ | 15 |
| Lemur | Pcoq | ATAPPFPGRPLSFPGQVCANDSDTLELPDRSRALLLGWVPT RLVPALYGLVLAVGLPANALALWVLAAK | 20 |
| human | Hsap | 37-DSTPSILPAPRGYPGQVCANDSDTLELPDSSRALLLGWVPT RLVPALYGLVLVVGLPANGLALWVLATQ | 15 |
| goat | Chir | GDDSTPRPHPRSFPGCPCANDSNTLELPPNSRALLLGWVPT KLVPALYGLVLAVGLPANSLALWVLATQ | 21 |
| human | Hsap | 37-DSTPSILPAPRGYPGQVCANDSDTLELPDSSRALLLGWVPT RLVPALYGLVLVVGLPANGLALWVLATQ | 15 |
| cat | Fcat | REGSPLPPKLRSFPGRPWANSSDEVEISDGSRALLLGWVPT RLVPALYGLTLLVGLPANGLALWVLATR | 22 |
| human | Hsap | 37-DSTPSILPAPRGYPGQVCANDSDTLELPDSSRALLLGWVPT RLVPALYGLVLVVGLPANGLALWVLATQ | 15 |
| dog | Clfa | QEGTPHSPHLRSFPGQPWANNSEILEIPESSRALLLGWVAT RLVPAVYGLALLVGLPANGLALWVLATR | 23 |
| human | Hsap | 37-DSTPSILPAPRGYPGQVCANDSDTLELPDSSRALLLGWVPT RLVPALYGLVLVVGLPANGLALWVLATQ | 15 |
| mouse | Mmus | EPKSSDKPNPRGYPGKFCANDSDTLELPASSQALLLGWVPT RLVPALYGLVVAVGLPANGLALWVLATR | 24 |
| human | Hsap | 37-DSTPSILPAPRGYPGQVCANDSDTLELPDSSRALLLGWVPT RLVPALYGLVLVVGLPANGLALWVLATQ | 15 |
| rat | Rnor | ESKSPDKPNPRGFPGKPCANNSDTLELPASSEALLLGWVPT RLVPAIYGLVVVVGLPANGLALWVLATR | 25 |
| human | Hsap | 37-DSTPSILPAPRGYPGQVCANDSDTLELPDSSRALLLGWVPT RLVPALYGLVLVVGLPANGLALWVLATQ | 15 |
| Collared flycatcher (bird) | Falb | PCPRAIPGDQARVNNVTYLLVPAYLLVPAGTRAQLGSAVTV RLIPGLYSLVLALGLPANALALRALAA- | 26 |
| human | Hsap | 37-DSTPSILPAPRGYPGQVCANDSDTLELPDSSRALLLGWVPT RLVPALYGLVLVVGLPANGLALWVLATQ | 15 |
| common carp | Ccar | RRGPL------------------P-SPTTLTLVVPLLYFLAFFIGLPTNLLALWVLLLQTKKLP | 27 |

There are a relatively small number of serine protease-generated functional PAR tethered ligands. Identifying the potentially diverse array of PAR tethered ligands may be important if they activate different cellular signaling pathways or vary by pathophysiologic conditions. In certain clinical settings, such as those with extensive platelet-neutrophil interactions or leukocytosis in malignancy, CatG may dampen or eliminate thrombin signaling through PAR1 and PAR4, while the CatG tethered ligand could induce persistent PAR4 signaling. PAR4 is also expressed in non-platelet tissues, where inflammation alters function and expression levels, and CatG could affect activation. Lastly, in hemorrhagic conditions, the RALLLGWVPTR (SEQ ID NO: 1) peptide could be therapeutic for rescuing or enhancing platelet reactivity.

\*\*\*

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A synthetic peptide mimetic comprising an amino acid sequence of SEQ ID NO: 1.

Clause 2. The synthetic peptide mimetic of clause 1, wherein the synthetic peptide mimetic induces activation of and signaling through PAR4.

Clause 3. The synthetic peptide mimetic of clause 1 or clause 2, wherein the synthetic peptide mimetic induces PAR4-dependent calcium flux.

Clause 4. The synthetic peptide mimetic of any one of clauses 1-3, wherein the synthetic peptide mimetic induces platelet aggregation.

Clause 5. The synthetic peptide mimetic of any one of clauses 1-4, wherein the synthetic peptide mimetic induces platelet activation.

Clause 6. A composition comprising the synthetic peptide mimetic of any one of clauses 1-5.

Clause 7. The composition of clause 6, wherein the composition further comprises a pharmaceutically acceptable carrier.

Clause 8. A method of treating a bleeding disorder, the method comprising administering to a subject a therapeutically effective amount of a synthetic peptide mimetic comprising an amino acid sequence of SEQ ID NO: 1.

Clause 9. The method of clause 8, wherein the synthetic peptide mimetic induces activation of and signaling through PAR4 in the subject.

Clause 10. The method of clause 8 or clause 9, wherein the synthetic peptide mimetic induces PAR4-dependent calcium flux in the subject.

Clause 11. The method of any one of clauses 8-10, wherein the synthetic peptide mimetic induces platelet aggregation in the subject.

Clause 12. The method of any one of clauses 8-11, wherein the synthetic peptide mimetic induces platelet activation in the subject.

Clause 13. The method of any one of clauses 8-12, wherein the bleeding disorder is hemophilia A (factor VIII deficiency), hemophilia B (factor IX deficiency), von Willebrand disease, thrombocytopenia, or bleeding due to qualitative platelet dysfunction.

Clause 14. The method of any one of clauses 8-13, wherein the bleeding disorder is a result caused by cirrhosis of the liver, leukemia, vitamin K deficiency, administration of aspirin, administration of heparin, or administration of warfarin.

```
                              SEQUENCES

SEQ ID NO: 1
11-mer PAR4 Tethered Ligand Fragment Amino Acid Sequence
RALLLGWVPTR SEQ ID NO: 2
10-mer PAR4 Tethered Ligand Fragment Amino Acid Sequence
ALLLGWVPTR SEQ ID NO: 3
8-mer PAR4 Tethered Ligand Fragment Amino Acid Sequence
RALLLGWV SEQ ID NO: 4
6-mer PAR4 Tethered Ligand Fragment Amino Acid Sequence
RALLLG SEQ ID NO: 5
6-mer Thrombin-Generated PAR4 Tethered Ligand Amino Acid Sequence
GYPGQV SEQ ID NO: 6
RC3 Monoclonal Antibody Target Amino Acid Sequence of PAR4
GDDSTPSILPAPRGYPGQVC SEQ ID NO: 7
PAR4-B Amino Acid Sequence
DDSTPSILPAPRGYPGQVCANDS SEQ ID NO: 8
PAR4-C Amino Acid Sequence
DSDTLELPDSSRALLLGWVPTR SEQ ID NO: 9
PAR4-C Fragment Amino Acid Sequence
DSDTLELPSS
```

| SEQUENCES |
| --- |
| SEQ ID NO: 10<br>Full Length Human PAR4 Amino Acid Sequence<br>MWGRLLLWPL VLGFSLSGGT QTPSVYDESG STGGGDDSTP SILPAPRGYP GQVCANDSDT<br>LELPDSSRAL LLGWVPTRLV PALYGLVLVV GLPANGLALW VLATQAPRLP STMLLMNLAT<br>ADLLLALALP PRIAYHLRGQ RWPFGEAACR LATAALYGHM YGSVLLLAAV SLDRYLALVH<br>PLRARALRGR RLALGLCMAA WLMAAALALP LTLQRQTFRL ARSDRVLCHD ALPLDAQASH<br>WQPAFTCLAL LGCFLPLLAM LLCYGATLHT LAASGRRYGH ALRLTAVVLA SAVAFFVPSN<br>LLLLLHYSDP SPSAWGNLYG AYVPSLALST LNSCVDPFIY YYVSAEFRDK VRAGLFQRSP<br>GDTVASKASA EGGSRGMGTH SSLLQ<br><br>SEQ ID NO: 11<br>12 Amino Acids Adjacent to Plasma Membrane of N-Terminal Human PAR4 Extracellular<br>Domain<br>SRALLLGWVPTR<br><br>SEQ ID NO: 12<br>12 Amino Acids Adjacent to Plasma Membrane of N-Terminal Dog PAR4 Extracellular Domain<br>SRALLLGWVATR<br><br>SEQ ID NO: 13<br>12 Amino Acids Adjacent to Plasma Membrane of N-Terminal Mouse PAR4 Extracellular<br>Domain<br>SQALLLGWVPTR<br><br>SEQ ID NO: 14<br>12 Amino Acids Adjacent to Plasma Membrane of N-Terminal Rat PAR4 Extracellular Domain<br>SEALLLGWVPTR<br><br>SEQ ID NO: 15<br>Human PAR4 Fragment Amino Acid Sequence<br>DSTPSILPAPRGYPGQVCANDSDTLELPDSSRALLLGWVPTRLVPALYGLVLVVGLPANGLAL<br>WVLATQ<br><br>SEQ ID NO: 16<br>Gorilla PAR4 Fragment Amino Acid Sequence<br>DSTPSILPAPRSYPGQVCANDSDTLELPDSSRALLLGWVPTRLVPALYGLVLVVGLPANGLALW<br>VLATQ<br><br>SEQ ID NO: 17<br>Olive Baboon PAR4 Fragment Amino Acid Sequence<br>DSTPSILPAPRGYPGQVCANDSDILELPDSSRALLLGWVPTRLVPALYGLVLAVGLPANGLALW<br>VLATR<br><br>SEQ ID NO: 18<br>Green Monkey PAR4 Fragment Amino Acid Sequence<br>ESTPSILPAPRGYPGQVCANDSDILELPDSSRALLLGWVPTRLVPALYGLVLAVGLPANSLALW<br>VLATR<br><br>SEQ ID NO: 19<br>North Greater Galago PAR4 Fragment Amino Acid Sequence<br>EATLLFPQQPRSFPGCVFTNNSDILEIPDSSRALLLGWVPTRLVPTLYGLVLVVGLPANGLALW<br>VLATQ<br><br>SEQ ID NO: 20<br>Lemur PAR4 Fragment Amino Acid Sequence<br>ATAPPFPGRPLSFPGQVCANDSDTLELPDRSRALLLGWVPTRLVPALYGLVLAVGLPANALAL<br>WVLAAK<br><br>SEQ ID NO: 21<br>Goat PAR4 Fragment Amino Acid Sequence<br>GDDSTPRPHPRSFPGCPCANDSNTLELPPNSRALLLGWVPTKLVPALYGLVLAVGLPANSLAL<br>WVLATQ<br><br>SEQ ID NO: 22<br>Cat PAR4 Fragment Amino Acid Sequence<br>REGSPLPPKLRSFPGRPWANSSDEVEISDGSRALLLGWVPTRLVPALYGLTLLVGLPANGLAL<br>WVLATR<br><br>SEQ ID NO: 23<br>Dog PAR4 Fragment Amino Acid Sequence<br>QEGTPHSPHLRSFPGQPWANNSEILEIPESSRALLLGWVATRLVPAVYGLALLVGLPANGLAL<br>WVLATR<br><br>SEQ ID NO: 24<br>Mouse PAR4 Fragment Amino Acid Sequence<br>EPKSSDKPNPRGYPGKFCANDSDTLELPASSQALLLGWVPTRLVPALYGLVVAVGLPANGLAL<br>WVLATR |

| SEQUENCES |
|---|

SEQ ID NO: 25
Rat PAR4 Fragment Amino Acid Sequence
ESKSPDKPNPRGFPGKPCANNSDTLELPASSEALLLGWVPTRLVPAIYGLVVVVGLPANGLAL
WVLATR SEQ ID NO: 26
Collared Flycatcher (Bird) PAR4 Fragment Amino Acid Sequence
PCPRAIPGDQARVNNVTYLLVPAYLLVPAGTRAQLGSAVTVRLIPGLYSLVLALGLPANALALRA
LAAX (X can be any amino acid residue, e.g., A, R, N, D, C, E, Q, G, H, I, L, K, M, F, P, S, T, W,
Y, or V)

SEQ ID NO: 27
Common Carp PAR4 Fragment Amino Acid Sequence
RRGPLXXXXXXXXXXXXXXXXXXXXPXSPTTLTLVVPLLYFLAFFIGLPTNLLALWVLLLQTKKLP
(X can be any amino acid residue, e.g., A, R, N, D, C, E, Q, G, H, I, L, K, M, F, P, S, T, W, Y, or
V)

SEQ ID NO: 28
PAR1 Activation Peptide Amino Acid Sequence
SFLLRN

SEQUENCE LISTING

```
Sequence total quantity: 28
SEQ ID NO: 1            moltype = AA  length = 11
FEATURE                 Location/Qualifiers
source                  1..11
                        mol_type = protein
                        organism = synthetic construct
SEQUENCE: 1
RALLLGWVPT R                                                              11

SEQ ID NO: 2            moltype = AA  length = 10
FEATURE                 Location/Qualifiers
source                  1..10
                        mol_type = protein
                        organism = synthetic construct
SEQUENCE: 2
ALLLGWVPTR                                                                10

SEQ ID NO: 3            moltype = AA  length = 8
FEATURE                 Location/Qualifiers
source                  1..8
                        mol_type = protein
                        organism = synthetic construct
SEQUENCE: 3
RALLLGWV                                                                  8

SEQ ID NO: 4            moltype = AA  length = 6
FEATURE                 Location/Qualifiers
source                  1..6
                        mol_type = protein
                        organism = synthetic construct
SEQUENCE: 4
RALLLG                                                                    6

SEQ ID NO: 5            moltype = AA  length = 6
FEATURE                 Location/Qualifiers
source                  1..6
                        mol_type = protein
                        organism = synthetic construct
SEQUENCE: 5
GYPGQV                                                                    6

SEQ ID NO: 6            moltype = AA  length = 20
FEATURE                 Location/Qualifiers
source                  1..20
                        mol_type = protein
                        organism = synthetic construct
SEQUENCE: 6
GDDSTPSILP APRGYPGQVC                                                     20
```

```
SEQ ID NO: 7              moltype = AA   length = 23
FEATURE                   Location/Qualifiers
source                    1..23
                          mol_type = protein
                          organism = synthetic construct
SEQUENCE: 7
DDSTPSILPA PRGYPGQVCA NDS                                              23

SEQ ID NO: 8              moltype = AA   length = 22
FEATURE                   Location/Qualifiers
source                    1..22
                          mol_type = protein
                          organism = synthetic construct
SEQUENCE: 8
DSDTLELPDS SRALLLGWVP TR                                               22

SEQ ID NO: 9              moltype = AA   length = 10
FEATURE                   Location/Qualifiers
source                    1..10
                          mol_type = protein
                          organism = synthetic construct
SEQUENCE: 9
DSDTLELPSS                                                             10

SEQ ID NO: 10             moltype = AA   length = 385
FEATURE                   Location/Qualifiers
source                    1..385
                          mol_type = protein
                          organism = synthetic construct
SEQUENCE: 10
MWGRLLLWPL VLGFSLSGGT QTPSVYDESG STGGGDDSTP SILPAPRGYP GQVCANDSDT       60
LELPDSSRAL LLGWVPTRLV PALYGLVLVV GLPANGLALW VLATQAPRLP STMLLMNLAT      120
ADLLLALALP PRIAYHLRGQ RWPFGEAACR LATAALYGHM YGSVLLLAAV SLDRYLALVH      180
PLRARALRGR RLALGLCMAA WLMAAALALP LTLQRQTFRL ARSDRVLCHD ALPLDAQASH      240
WQPAFTCLAL LGCFLPLLAM LLCYGATLHT LAASGRRYGH ALRLTAVVLA SAVAFFVPSN      300
LLLLLHYSDP SPSAWGNLYG AYVPSLALST LNSCVDPFIY YVVSAEFRDK VRAGLFQRSP      360
GDTVASKASA EGGSRGMGTH SSLLQ                                           385

SEQ ID NO: 11             moltype = AA   length = 12
FEATURE                   Location/Qualifiers
source                    1..12
                          mol_type = protein
                          organism = synthetic construct
SEQUENCE: 11
SRALLLGWVP TR                                                          12

SEQ ID NO: 12             moltype = AA   length = 12
FEATURE                   Location/Qualifiers
source                    1..12
                          mol_type = protein
                          organism = synthetic construct
SEQUENCE: 12
SRALLLGWVA TR                                                          12

SEQ ID NO: 13             moltype = AA   length = 12
FEATURE                   Location/Qualifiers
source                    1..12
                          mol_type = protein
                          organism = synthetic construct
SEQUENCE: 13
SQALLLGWVP TR                                                          12

SEQ ID NO: 14             moltype = AA   length = 12
FEATURE                   Location/Qualifiers
source                    1..12
                          mol_type = protein
                          organism = synthetic construct
SEQUENCE: 14
SEALLLGWVP TR                                                          12

SEQ ID NO: 15             moltype = AA   length = 69
FEATURE                   Location/Qualifiers
source                    1..69
                          mol_type = protein
                          organism = synthetic construct
SEQUENCE: 15
DSTPSILPAP RGYPGQVCAN DSDTLELPDS SRALLLGWVP TRLVPALYGL VLVVGLPANG       60
LALWVLATQ                                                              69
```

```
SEQ ID NO: 16            moltype = AA   length = 69
FEATURE                  Location/Qualifiers
source                   1..69
                         mol_type = protein
                         organism = synthetic construct
SEQUENCE: 16
DSTPSILPAP RSYPGQVCAN DSDTLELPDS SRALLLGWVP TRLVPALYGL VLVVGLPANG    60
LALWVLATQ                                                           69

SEQ ID NO: 17            moltype = AA   length = 69
FEATURE                  Location/Qualifiers
source                   1..69
                         mol_type = protein
                         organism = synthetic construct
SEQUENCE: 17
DSTPSILPAP RGYPGQVCAN DSDILELPDS SRALLLGWVP TRLVPALYGL VLAVGLPANG    60
LALWVLATR                                                           69

SEQ ID NO: 18            moltype = AA   length = 69
FEATURE                  Location/Qualifiers
source                   1..69
                         mol_type = protein
                         organism = synthetic construct
SEQUENCE: 18
ESTPSILPAP RGYPGQVCAN DSDILELPDS SRALLLGWVP TRLVPALYGL VLAVGLPANS    60
LALWVLATR                                                           69

SEQ ID NO: 19            moltype = AA   length = 69
FEATURE                  Location/Qualifiers
source                   1..69
                         mol_type = protein
                         organism = synthetic construct
SEQUENCE: 19
EATLLFPQQP RSFPGCVFTN NSDILEIPDS SRALLLGWVP TRLVPTLYGL VLVVGLPANG    60
LALWVLATQ                                                           69

SEQ ID NO: 20            moltype = AA   length = 69
FEATURE                  Location/Qualifiers
source                   1..69
                         mol_type = protein
                         organism = synthetic construct
SEQUENCE: 20
ATAPPFPGRP LSFPGQVCAN DSDTLELPDR SRALLLGWVP TRLVPALYGL VLAVGLPANA    60
LALWVLAAK                                                           69

SEQ ID NO: 21            moltype = AA   length = 69
FEATURE                  Location/Qualifiers
source                   1..69
                         mol_type = protein
                         organism = synthetic construct
SEQUENCE: 21
GDDSTPRPHP RSFPGCPCAN DSNTLELPPN SRALLLGWVP TKLVPALYGL VLAVGLPANS    60
LALWVLATQ                                                           69

SEQ ID NO: 22            moltype = AA   length = 69
FEATURE                  Location/Qualifiers
source                   1..69
                         mol_type = protein
                         organism = synthetic construct
SEQUENCE: 22
REGSPLPPKL RSFPGRPWAN SSDEVEISDG SRALLLGWVP TRLVPALYGL TLLVGLPANG    60
LALWVLATR                                                           69

SEQ ID NO: 23            moltype = AA   length = 69
FEATURE                  Location/Qualifiers
source                   1..69
                         mol_type = protein
                         organism = synthetic construct
SEQUENCE: 23
QEGTPHSPHL RSFPGQPWAN NSEILEIPES SRALLLGWVA TRLVPAVYGL ALLVGLPANG    60
LALWVLATR                                                           69

SEQ ID NO: 24            moltype = AA   length = 69
FEATURE                  Location/Qualifiers
source                   1..69
                         mol_type = protein
                         organism = synthetic construct
```

```
SEQUENCE: 24
EPKSSDKPNP RGYPGKFCAN DSDTLELPAS SQALLLGWVP TRLVPALYGL VVAVGLPANG    60
LALWVLATR                                                            69

SEQ ID NO: 25          moltype = AA  length = 69
FEATURE                Location/Qualifiers
source                 1..69
                       mol_type = protein
                       organism = synthetic construct
SEQUENCE: 25
ESKSPDKPNP RGFPGKPCAN NSDTLELPAS SEALLLGWVP TRLVPAIYGL VVVVGLPANG    60
LALWVLATR                                                            69

SEQ ID NO: 26          moltype = AA  length = 69
FEATURE                Location/Qualifiers
source                 1..69
                       mol_type = protein
                       organism = synthetic construct
VARIANT                69
                       note = X can be any amino acid residue, e.g., A, R, N, D,
                       C, E, Q, G, H, I, L, K, M, F, P, S, T, W, Y, or V
SEQUENCE: 26
PCPRAIPGDQ ARVNNVTYLL VPAYLLVPAG TRAQLGSAVT VRLIPGLYSL VLALGLPANA    60
LALRALAAX                                                            69

SEQ ID NO: 27          moltype = AA  length = 65
FEATURE                Location/Qualifiers
source                 1..65
                       mol_type = protein
                       organism = synthetic construct
VARIANT                6..24
                       note = X can be any amino acid residue, e.g., A, R, N, D,
                       C, E, Q, G, H, I, L, K, M, F, P, S, T, W, Y, or V
VARIANT                26
                       note = X can be any amino acid residue, e.g., A, R, N, D,
                       C, E, Q, G, H, I, L, K, M, F, P, S, T, W, Y, or V
SEQUENCE: 27
RRGPLXXXXX XXXXXXXXXX XXXXPXSPTT LTLVVPLLYF LAFFIGLPTN LLALWVLLLQ    60
TKKLP                                                                65

SEQ ID NO: 28          moltype = AA  length = 6
FEATURE                Location/Qualifiers
source                 1..6
                       mol_type = protein
                       organism = synthetic construct
SEQUENCE: 28
SFLLRN                                                                6
```

The invention claimed is:

1. A synthetic peptide mimetic consisting of SEQ ID NO: 1, wherein the synthetic peptide mimetic induces activation of and signaling through PAR4.

2. The synthetic peptide mimetic of claim 1, wherein the synthetic peptide mimetic induces PAR4-dependent calcium flux.

3. The synthetic peptide mimetic of claim 1, wherein the synthetic peptide mimetic induces platelet aggregation.

4. The synthetic peptide mimetic of claim 1, wherein the synthetic peptide mimetic induces platelet activation.

5. A composition comprising the synthetic peptide mimetic of claim 1.

6. The composition of claim 5, wherein the composition further comprises a pharmaceutically acceptable carrier.

7. A method of treating a bleeding disorder, the method comprising administering to a subject a therapeutically effective amount of a synthetic peptide mimetic consisting of SEQ ID NO: 1.

8. The method of claim 7, wherein the synthetic peptide mimetic induces activation of and signaling through PAR4 in the subject.

9. The method of claim 7, wherein the synthetic peptide mimetic induces PAR4-dependent calcium flux in the subject.

10. The method of claim 7, wherein the synthetic peptide mimetic induces platelet aggregation in the subject.

11. The method of claim 7, wherein the synthetic peptide mimetic induces platelet activation in the subject.

12. The method of claim 7, wherein the bleeding disorder is hemophilia A (factor VIII deficiency), hemophilia B (factor IX deficiency), von Willebrand disease, thrombocytopenia, or bleeding due to qualitative platelet dysfunction.

13. The method of claim 7, wherein the bleeding disorder is a result caused by cirrhosis of the liver, leukemia, vitamin K deficiency, administration of aspirin, administration of heparin, or administration of warfarin.

* * * * *